(12) United States Patent
Verma et al.

(10) Patent No.: US 9,833,300 B2
(45) Date of Patent: Dec. 5, 2017

(54) DENTAL IMPLANT SYSTEM

(75) Inventors: Mahesh Verma, New Delhi (IN);
Naresh Bhatnagar, New Delhi (IN);
Abhinav Sood, New Delhi (IN);
Farukh Faraz, New Delhi (IN);
Kshitij Sharma, New Delhi (IN);
Gedela V. Rao, New Delhi (IN); Palani S. Kumar, New Delhi (IN); Shankar Iyer, Elizabeth, NJ (US)

(73) Assignee: Council of Scientific & Industrial Research, New Delhi (IN)

( * ) Notice: Subject to any disclaimer, the term of this patent is extended or adjusted under 35 U.S.C. 154(b) by 188 days.

(21) Appl. No.: 12/739,654

(22) PCT Filed: Oct. 23, 2008

(86) PCT No.: PCT/IN2008/000700
§ 371 (c)(1),
(2), (4) Date: Jan. 28, 2011

(87) PCT Pub. No.: WO2009/054005
PCT Pub. Date: Apr. 30, 2009

(65) Prior Publication Data
US 2011/0117522 A1 May 19, 2011

(30) Foreign Application Priority Data
Oct. 26, 2007 (IN) ............................ 2243/DEL/2007

(51) Int. Cl.
*A61C 8/00* (2006.01)
(52) U.S. Cl.
CPC ............ *A61C 8/005* (2013.01); *A61C 8/0022* (2013.01); *A61C 8/0025* (2013.01);
(Continued)

(58) Field of Classification Search
CPC ...................................... A61C 8/0048–8/0078
(Continued)

(56) References Cited

U.S. PATENT DOCUMENTS 5,588,838 A * 12/1996 Hansson ............. A61C 8/0022
433/173
6,149,432 A * 11/2000 Shaw et al. .................. 433/174
(Continued)

FOREIGN PATENT DOCUMENTS

| WO | WO 03/030767 A | 4/2003 |
| WO | WO 2006/081239 A | 8/2006 |
| WO | WO 2007/022655 A | 3/2007 |

OTHER PUBLICATIONS

Eskitascioglu et al., "The influence of occlusal loading location on stresses transferred to implant-supported prostheses and supporting bone: a three-dimensional finite element study," Feb. 2004, Journal of Prosthetic Dentistry, vol. 91, pp. 144-150.*

*Primary Examiner* — Matthew Nelson
(74) *Attorney, Agent, or Firm* — Locke Lord LLP; Daniel J. Fiorello; Joshua L. Jones

(57) ABSTRACT

A screw type dental implant system (1), having a dental implant fixture (2), a multifunctional component (3) and an abutment screw (4). The screw shape dental implant fixture has an external surface having buttress threads on the body and micro threads at the collar. This combination provides the advantages of: improved biomechanics at the implant abutment interface, self-tapping nature to the implant, and minimizing the stresses at the crest of the bone leading to decrease resorption of crestal bone. The multifunctional component serves the purposes of implant mount, impression analog and final abutment and has a single prosthetic platform so one component is compatible with different implant dimensions, which minimizes the inventory needed for the implant system and allows easy handling of the (Continued)

system. The multifunctional component also has an external concave transmucosal portion for enhancing the emergence profile and internal threads for securing the abutment screw.

33 Claims, 20 Drawing Sheets

(52) U.S. Cl.
CPC .......... *A61C 8/0069* (2013.01); *A61C 8/0001* (2013.01); *A61C 8/006* (2013.01); *A61C 8/0068* (2013.01); *A61C 8/0078* (2013.01)

(58) Field of Classification Search
USPC ........................................ 433/172–176, 201.1
See application file for complete search history.

(56) References Cited

U.S. PATENT DOCUMENTS

| | | | | |
|---|---|---|---|---|
| 6,358,052 | B1* | 3/2002 | Lustig | A61C 8/0001 433/174 |
| 6,733,291 | B1* | 5/2004 | Hurson | A61C 8/0054 433/173 |
| 6,981,873 | B2* | 1/2006 | Choi et al. | 433/173 |
| 7,014,464 | B2* | 3/2006 | Niznick | A61C 8/0001 433/173 |
| 7,104,797 | B2* | 9/2006 | Rassoli | 433/173 |
| 2003/0082498 | A1* | 5/2003 | Halldin et al. | 433/173 |
| 2004/0006346 | A1* | 1/2004 | Holmen | A61C 8/0025 433/173 |
| 2004/0142304 | A1 | 7/2004 | Cottrell | |
| 2005/0037319 | A1* | 2/2005 | Bulard et al. | 433/173 |
| 2005/0191600 | A1* | 9/2005 | Beaty et al. | 433/173 |
| 2005/0214714 | A1* | 9/2005 | Wohrle | 433/173 |
| 2006/0172257 | A1* | 8/2006 | Niznick | A61C 8/0022 433/173 |
| 2006/0223030 | A1* | 10/2006 | Dinkelacker | 433/174 |
| 2007/0037123 | A1* | 2/2007 | Mansueto | A61C 8/0022 433/173 |
| 2007/0072150 | A1* | 3/2007 | Mansueto | A61C 8/0022 433/174 |
| 2007/0298379 | A1* | 12/2007 | D'Alise | A61C 8/0025 433/174 |
| 2008/0261176 | A1* | 10/2008 | Hurson | A61C 8/0022 433/174 |

* cited by examiner

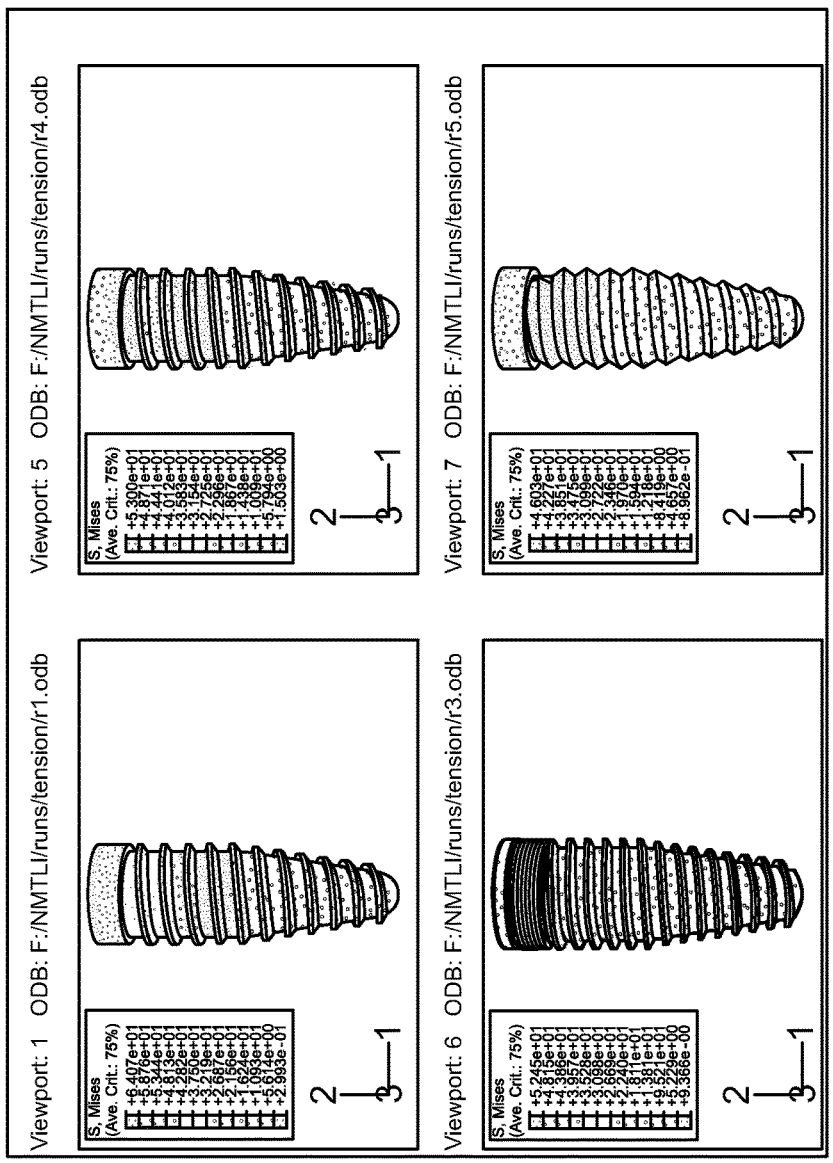

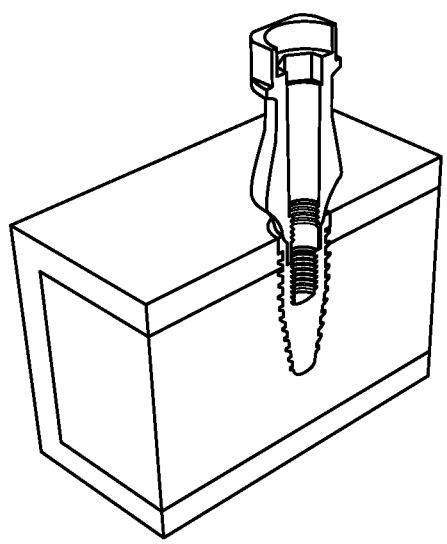
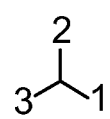
FIG. 16

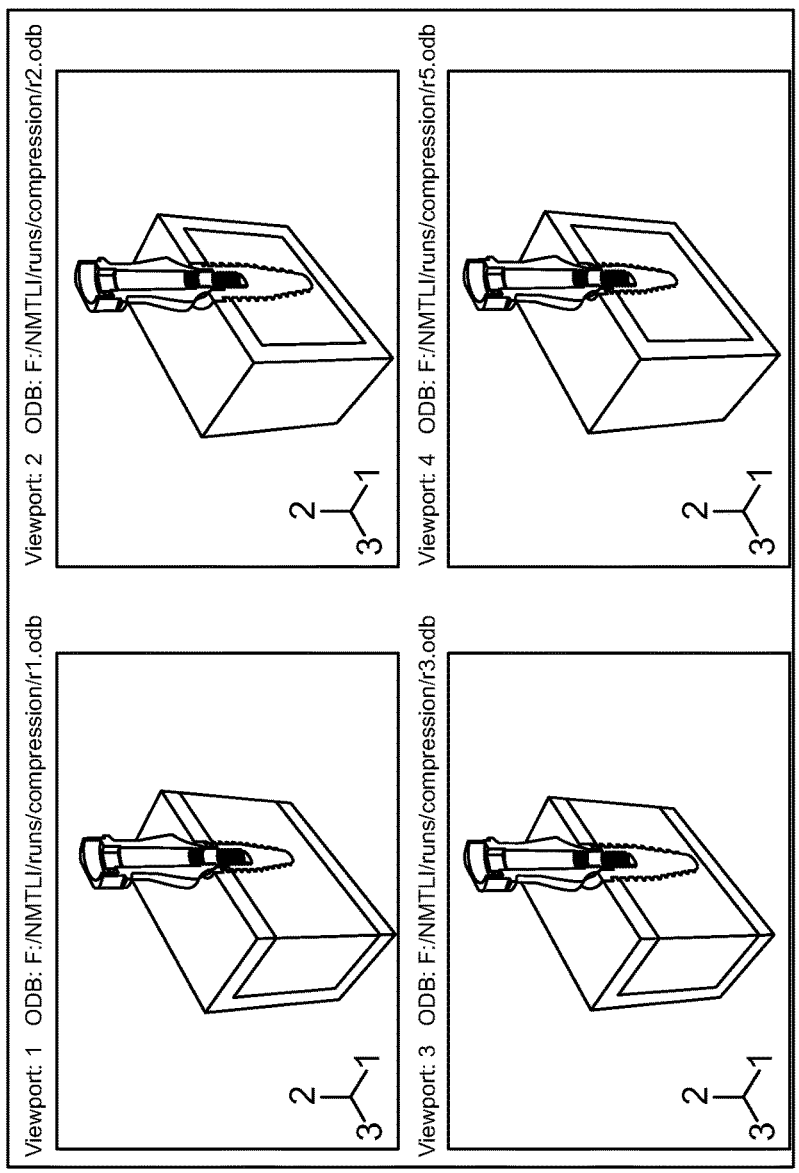

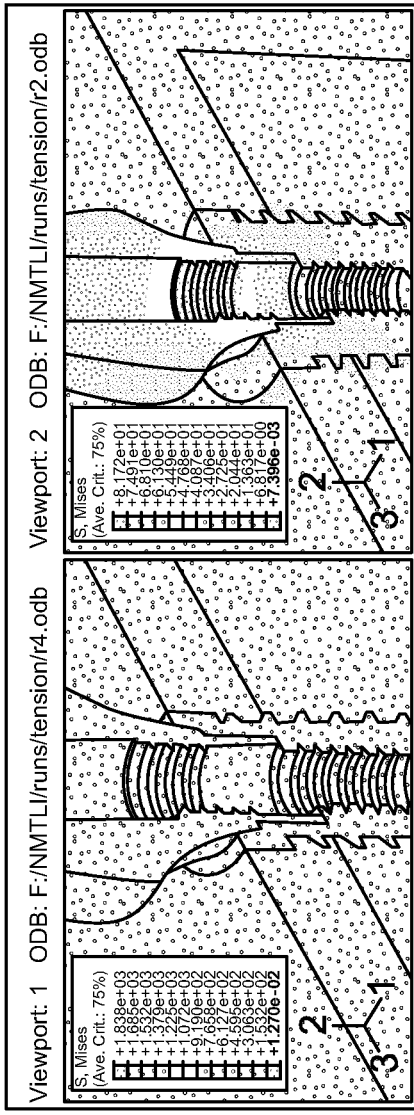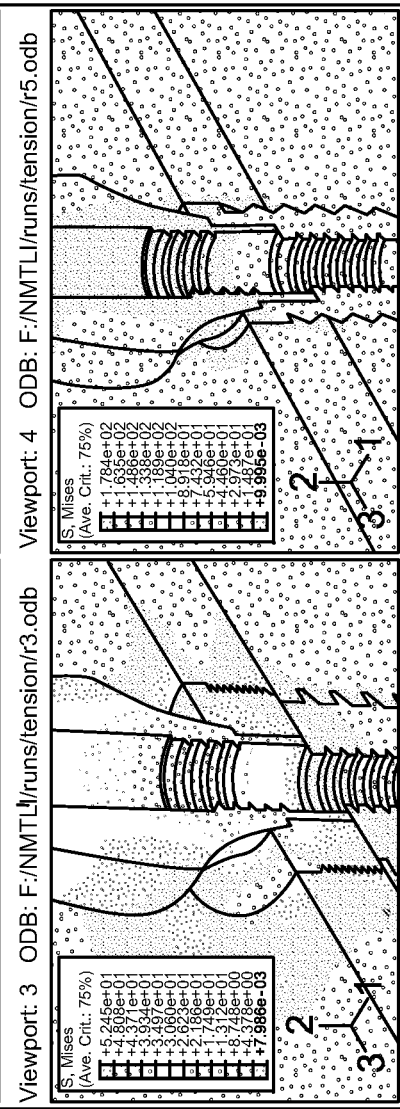
FIG. 22(A)  FIG. 22(B)  FIG. 22(C)  FIG. 22(D)

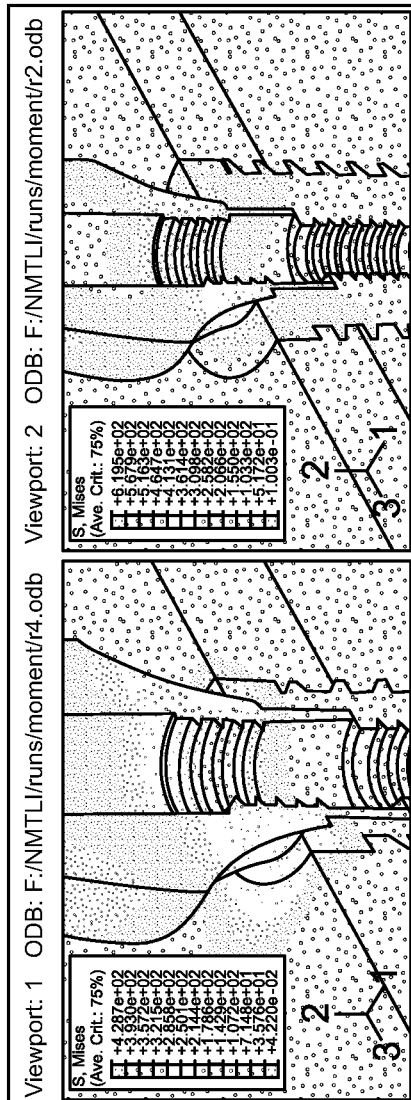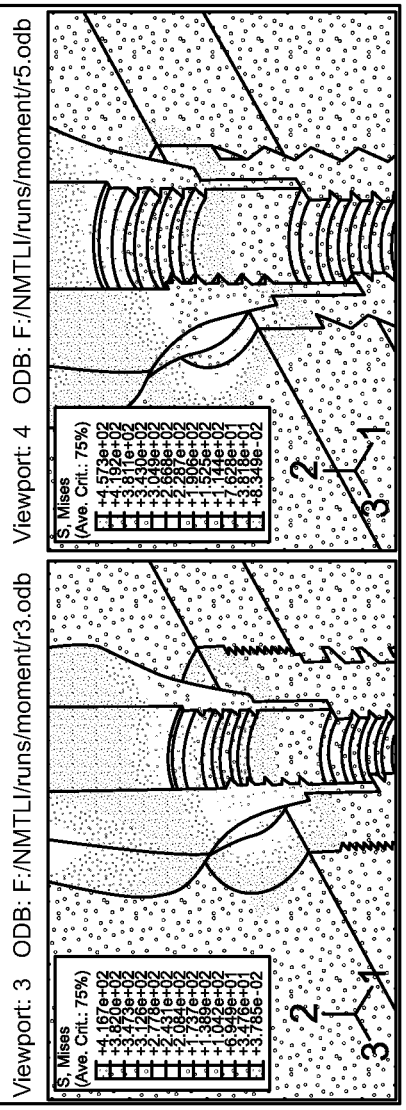
FIG. 23(A)  FIG. 23(B)  FIG. 23(C)  FIG. 23(D)

DENTAL IMPLANT SYSTEM

CROSS REFERENCE TO RELATED APPLICATIONS

This application is a U.S. National Stage application under 35 U.S.C. §371 of International Patent Application Serial No. PCT/IN2008/000700, filed Oct. 23, 2008 and Amended Under PCT Article 19 on Oct. 28, 2009 which claims the benefit of the Indian Patent Application No. 2243/DEL/2007, filed Oct. 26, 2007, the disclosures of each of which are expressly incorporated by reference in their entireties.

FIELD OF THE INVENTION

The present invention relates to a dental implant system that supports a prosthetic device, for replacing the missing natural teeth. A unique dental implant system is introduced in the invention, which overcomes most of the shortcomings of the present dental implant systems in the market. The different components of the dental implant system have the combined advantages of enhanced stability due to improved biomechanics at the implant abutment interface and better preservation of alveolar bone; ease of placement; favorable esthetics; minimal inventory; ease of handling and cost effectiveness. The dental implant system comprises of three components namely—Dental implant fixture, Multifunctional component and the Abutment screw.

BACKGROUND AND PRIOR ART OF THE INVENTION

Natural teeth may be lost as a result of dental diseases or trauma making it desirable for replacement with prosthetic devices. One type of prosthetic device is a dental implant or root member, which is surgically positioned within the mandibular or maxillary alveolar bone. After healing a head member or abutment is mounted on the implant and then, in turn, a tooth simulating prosthesis, or crown, is mounted on the abutment.

Ravindernath and Mehta devised a dental implant comprising an implant base body for implantation in the pre-drilled whole in the jaw bone of the patient and a head member adapted to be interconnected with the said base body being provided for supporting prosthetic device for any tooth/teeth structure. The said implant base body has a flat top surface a conical and tapered lower end terminating in a flat base, a circular boundary and a parallel, non tapered sides extending from the top to the bottom. The said head member has a top surface and a bottom surface joined together through a straight parallel sides extending from the top to the bottom end of the shaft (INDIAN PATENT NUMBER 401/DEL/94). Another patent (INDIAN PATENT NUMBER 403/DEL/94) from the same inventors discloses a surgical dental implant, comprising a partly threaded cylindrical root member to be implanted in a predrilled bone of the jaw and to be interconnected with the head member, said root member has a flat top surface and a conical bottom end and said head member has a body part mounted on a shaft part. The drawbacks of the invention are its complete cylindrical shape which requires more bone removal and pressure during implant placement, crude thread design, non-self tapping threads, and no micro threads for crestal bone preservation.

U.S. Pat. No. 4,826,434 discloses a dental implant that can be constructed out of titanium so as to have a first end for insertion into a jawbone, an externally threaded shank extending from said first end, a tapered head on said shank adjacent to the second end of the implant and an internally threaded bore shape so as to include a non-round socket in the threads of said bore.

U.S. Pat. No. 5,061,181 discloses a dental implant anchor which includes a body portion having a first external wall portion carrying one or more circumferential projections separated by circumferential grooves and, below, a second external wall portion carrying threads. In some forms, the anchor also includes one or more longitudinally oriented grooves on its exterior wall. This invention does not have micro threads at the collar and the implant is partially threaded. Thus leading to limited crestal bone preservation and reduced primary stability for proper osseointegration of the implant with bone.

U.S. Pat. No. 5,064,425 discloses an elongate cylindrical body member adapted for permanent anchoring of its lower end into bone tissue and constructed to support an attached device such as a tooth at its upper end. The body member has an external screw thread formed in its outer surface, and at least one cavity defined therein adjacent to its bottom end. Each cavity forms at its intersection with the screw thread at least one cutting edge for self-tapping as the body member is screwed into the bone tissue. U.S. Pat. No. 5,312,256 discloses a dental implant which has a cylindrical body, with a rounded apical end. The cylindrical body has a succession of alternate flat parts and externally screw-threaded parts extending lengthwise of the body of the implant. There are two wide threaded parts for self-tapping and/or retention in already-tapped bone and two narrow threaded parts serving as guide rails during impacting and permitting the escape of chips during self-tapping. U.S. Pat. No. 5,727,943 discloses a self-tapping dental implant comprising a generally cylindrical body with a threaded outer surface. The cylindrical body has a plurality of longitudinal recesses formed in the threaded surface at one end and extends longitudinally through a plurality of turns of the thread to form a self-tapping cutting edge at each interruption of the thread by one of the recesses. The main drawbacks of the above inventions are their complete cylindrical shape which requires more bone removal during implant placement, limited self tapping nature of the threads, and no microthreads for crestal bone preservation.

U.S. Pat. No. 5,816,812 discloses a self-tapping dental prosthetic implant which has a blunt leading end, a tapered first section which has a uniform minor diameter and a uniformly increasing major diameter, a second section having uniform minor and major thread diameters, a third section with a uniform major thread diameter and a outwardly tapering minor diameter and a fourth section which has a diameter larger than any other segment and a relatively low profile (i.e., short axial length). A thread-cutting groove extends over a substantial portion of the threaded length of the implant.

U.S. Pat. No. 5,007,835 discloses a screw-typed dental implant which is featured having rounded threads for providing a controlled radial osteocompressive force against the threaded wall of bone tissue that was previously drilled and tapped. The thread profile provided by the tap is undercut below the external thread surface of the implant causing a compressive force to be exerted against the bone wall. The main drawbacks of the invention was the lower primary stability for proper osseointegration as the engagement with the bone was decreased due to the round shape of the threads and higher shear forces at the bone implant interface.

U.S. Pat. No. 5,074,790 discloses a screw implant for a jawbone that has a conical threaded implant body. The thread of the implant body is a compression thread with concave thread turns. The main drawback of the invention was the lower primary stability for proper osseo integration as the engagement with the bone was decreased due to the round shape of the threads. Higher shear forces at the bone implant interface.

U.S. Pat. No. 4,406,623 discloses a screw-type bone implant having a shaft with V-shape threads, particular length and the design of its free end, which helps its support between two ends by compact bone. Thus the implant offers a permanent and particularly secure support for a dental prosthesis. The disadvantages of the V-shape threads were development of high shear component of the axial load at the bone implant interface, which leads to faster loss of bone at the interface during function.

U.S. Pat. No. 5,823,777 discloses a dental implant having selected thread feature that could include the minor diameter, the thread pitch or the thread geometry (square threads). The selected biomedical characteristic is one of the locations in the bone in which the implant is placed, the elastic modulus of the bone and the desired biomechanical response of the bone. The disadvantages of the square thread design are the non-self tapping nature leading to more forces at the bone during insertion of the implant. This hampers the healing process after implant placement.

U.S. Pat. No. 5,601,429 discloses an anchor for a dental implant which preferably comprises of buttress type threads with a pitched relief groove extends across all convolutions of the external, self-tapping threads. The pitch of the relief groove is angled to vary from that of the threads, so that the groove intersects all threads, but the pitch is inclined in the same direction as that of the threads. The groove thus complements screwing action of the self-tapping thread. This invention utilizes the advantage of buttress threads however does not incorporate the microthreads at the collar which can reduce the crestal bone loss.

Reference may be made to U.S. Pat. No. 5,816,813 wherein an invention related to an implant having a body with at least one generally cylindrical part to be implanted into bone tissue is disclosed. The cylindrical part is at least partly provided with threads having a height between 0.02 mm and 0.20 mm. U.S. Pat. No. 6,419,491 discloses a dental implant system which includes an implant element for surgical insertion into a maxillofacial bone or tissue of a patient, the implant element having a collar section and a distal, anchor-like section, the collar section having an ordered microgeometric repetitive surface pattern in the form of alternating ridges and grooves, each having a fixed or established width in a range of about 2.0 to about 25 microns (micrometers) and a fixed or established depth in a range of about 2 to about 25 microns, in which the microgeometric repetitive patterns define a guide for preferential promotion of the rate, orientation and direction of growth colonies of cells of the maxillofacial bone or tissue which are in contact with the surface pattern.

U.S. Pat. No. 6,083,004 discloses an abutment-mount for a dental implant that has a longitudinally extending axis with a first end, an opposite second end and a peripheral surface. The abutment-mount is used for delivering the dental implant to a prepared site of a jawbone with an implant drive tool and is also used as a device for securing a dental prosthesis to the dental implant. The abutment-mount includes a screw, or other fastener for securing the abutment-mount to the implant. A surface is provided for attaching the dental prosthesis to the abutment-mount adjacent the first end. A structure is provided for transferring rotational force from the implant drive tool to the implant through the abutment-mount. An implant kit includes an abutment-mount, an implant and an abutment screw U.S. Pat. No. 7,137,816 discloses that fixture mount limits torque that may be applied when installing a dental implant and also serves as an impression post and an abutment for a temporary prosthesis. In preferred embodiments, the fixture mount is formed of plastic and is subject to chair side modifications by the surgeon so as to be better suited as an abutment. Methods of shaping the fixture mount for use as an abutment and for making a dental restoration using the shaped abutment are disclosed.

Histologic and radiographic observations suggest that a biologic dimension of hard and soft tissues exists around dental implants and extends apically from the implant-abutment interface. Radiographic evidence of the development of the biologic dimension can be demonstrated by the vertical repositioning of crestal bone and the subsequent soft tissue attachment to the implant that occurs when an implant is uncovered and exposed to the oral environment and matching-diameter restorative components are attached. Historically, two-piece dental implant systems have been restored with prosthetic components that locate the interface between the implant and the attached component element at the outer edge of the implant platform. In 1991, Implant Innovations introduced wide-diameter implants with matching wide-diameter platforms. When introduced, however, matching-diameter prosthetic components were not available, and many of the early 5.0- and 6.0-mm-wide implants received "standard"-diameter (4.1-mm) healing abutments and were restored with "standard"-diameter (4.1-mm) prosthetic components. Long-term radiographic follow-up of these "platform-switched" restored wide-diameter dental implants has demonstrated a smaller than expected vertical change in the crestal bone height around these implants than is typically observed around implants restored conventionally with prosthetic components of matching diameters. This radiographic observation suggests that the resulting post restorative biologic process resulting in the loss of crestal bone height is altered when the outer edge of the implant-abutment interface is horizontally repositioned inwardly and away from the outer edge of the implant platform. This article introduces the concept of platform switching and provides a foundation for future development of the biologic understanding of the observed radiographic findings and clinical rationale for this technique (Lazzara and Porter, 2006).

Frost (1992) has proposed the hypothesis that bone cells respond to a local deformation of the bone produced by mechanical stress. The bone adapts to a certain strain—in a steady state. With slightly increased strain, the bone becomes mildly overloaded and compensates by forming more bone. If the strain goes beyond a threshold which exceeds the bone's capacity fatigue fracture can occur.

Typically a bone is believed to function within the strain range of approximately 50-1500 microstrain (Frost 2004). If the peak load on a bone results in strains of 1500-3000 microstrain a mild overload occurs. According to Frost's hypothesis (Frost 1992, 2004), this can result in mechanical fatigue damage, but remodeling normally repairs the damage and thus prevents it accumulating. Loads influencing the bone in this interval may even result in an osseous adaptation by formation of bone (reshaping and strengthening), presumably to reduce the future functional strain within the bone. Overloading the bone can increase the micro-damage (and the repair). Repeated stress on the bone resulting in deformations greater than 3000 microstrain increase the micro-damage. Such deformations can overwhelm the repair mechanism and result in a fatigue failure. In comparison, normal bone fractures suddenly at forces causing a deformation of about 2.5% (25,000 microstrain).

In contrast, if the strain in the bone does not exceed 50-100 microstrain, disuse of the bone occurs and remodeling results in a net loss of bone. Thus, a moderate increase from the optimal functional strains induces an increase in bone mass that, if the loading remains constant, re-establishes new optimal strains. Conversely, where functional loading is reduced to a level where optimal strains are not achieved, bone loss occurs to adapt to the new demand (Frost 1992).

It is important to appreciate that in this theory it is not the actual load that is important but the effect of the load on the bone—the resulting strain in the bone. This also depends on the amount of bone tissue. According to Frost (2004) a load of 1-2 MPa (approximately equivalent to 0.1-0.2 kg/mm$^2$) results in 50-100 microstrain in cortical lamellar bone in healthy young adult mammals, and 60 MPa in 3000 microstrain. The level for sudden fracture is 25,000 microstrain and is obtained with a stress of 120 MPa. It has been suggested that there is not always a linear relationship between stress and bone failure, with one group reporting that a doubling of the stress that originally caused 2000 microstrain increased the microscopic fatigue damage in bone by 400 times (Pattin et al. 1996).

The stability of the dental implant system depends upon the biomechanical integrity of the components of the implant system and the support provided by the alveolar bone of the jaws. The biomechanical integrity of the components at the implant abutment interface and the alveolar bone level maintenance can be achieved by appropriate implant design. One of the aspects of implant design is the topography of the implant and the thread design.

Prior art has shown implant bodies mostly with cylindrical shape (Indian Patent No: 401/DEL/94 and 403/DEL/94; U.S. Pat. Nos. 5,312,256 and 5,727,943). However the cylindrical design has the disadvantages of causing excessive pressure on bone during insertion and unnecessary removal of bone for insertion. In the present invention the screw implants are made with the upper cylindrical portion and lower tapering portion to have the advantages of self-tapping, easy insertion in the bone, no excessive pressure at the implant bone junction, simulation of the natural anatomy of the root portion of the tooth, and avoiding injury to anatomical structures.

The implants with smooth and stepped topography does not obtain the desired postoperative primary stability, cannot maintain the alveolar bone level because of the stress shielding effect i.e. insufficient introduction of force to the bone for remodeling and have more shearing forces at the bone level under functional axial loading. The screw implants having external threaded surface have increased surface area which enhances osseointegrated bone implant contact level, have lower stress-shielding effect thus induces better remodeling of bone around implants, favorably transforms and distributes the shearing forces at the bone implant interface and better primary stability.

Thread shape is one of the most important factors which affects the forces applied on the bone and implant system during insertion and function. Prior art has revealed the use of different types of threaded designs like Standard V shape threads, Square shape threads, Buttress shape threads and Reverse Buttress threads (U.S. Pat. Nos. 4,406,623, 5,823,777 and 5,601,429). The comparison of these threads are made depending upon the—

1) location of stresses i.e. at the crest of alveolar bone and in the implant system under different type of loading forces,
2) transformation of axial loads into shearing component at the bone implant interface, and
3) Self-tapping nature.

Standard V shape threads produce high shearing component of the axial load at the bone implant interface, thus leads to faster bone loss at the interface during function.

Square shape threads and reverse buttress threads have non-self tapping nature so produce increased forces during insertion at the bone implant interface, thus can lead to resorption of the bone affecting osseointegration process and stability of implant.

To overcome these limitations buttress threads are incorporated in the implant design to have self-tapping nature for easy insertion into the bone, transfer lesser functional forces at the implant abutment junction which is the most prone area for implant failure due to its lower strength, better primary stability, while producing moderate amount of forces at the alveolar crest during function under different type of forces and with comparable shearing component of the axial load at implant bone interface.

OBJECTS OF THE INVENTION

The primary objective of the present invention is to provide the surgical dental implant system capable of being machined and fabricated conveniently and economically, made up of any biologically inert metal and/or alloys thereof and to use the same on patients more conveniently, comfortably and being implanted in very short duration without causing trauma to the patient.

The objective of the present invention is to provide a screw dental implant with crestal module consisting of surface treated collar at the top for better soft tissue integration and micro roughness below for favorable distribution of forces at the crest of alveolar bone thus preserving and maintaining the alveolar bone for longer period of time.

The objective of the invention is to fabricate a screw dental implant with a unique combination of the buttress threads on the body of the implant and micro threads on the crestal module, which makes the implant self tapping, with reduced crestal bone loss and reduced forces at the critical implant abutment junction.

Another objective of the invention is to fabricate an implant system with rounded end apical portion to prevent damage to the vital structures and apical recess to allow the collection of the bone chips during the insertion of self-tapping dental implant in drilled site of jawbones The objective of the present invention is to minimize the inventory needed for the dental implant system by introducing the multifunctional component.

Another objective of the present invention is to introduce an implant system with the multifunctional component designed with the feature of single prosthetic platform. Thus one abutment is compatible with different implant dimensions.

Yet another object of the present invention concerns with a dental implant system, which provides better esthetics by incorporating an external concave transmucosal surface on the abutment, which provides the prosthesis with the natural emergence profile.

Yet another objective of the present invention concerns with a dental implant system with the abutment having threaded portion in the lower part of the internal channel which prevents the falling off of the abutment screw from the abutment after the screw is loosened from the implant channel.

Another objective of the present invention concerns with a dental implant system having an abutment screw with long head internal channel with the groove. Thus the tightening properties of the abutment screw can still be maintained even after the abutment and the screw is reduced for accommodating the prosthesis.

Yet another objective of the present invention is to incorporate the components with modernized technology yet making it economical and easy to use by minimizing the inventory.

SUMMARY OF THE INVENTION

The present invention relates to the fabrication of an endosseous dental implant system, which is intended to be surgically placed in the drilled bone site of the upper (maxillary) or lower (mandibular) jaw arches to provide support for prosthetic devices in the replacement of missing natural dentition.

The present invention also relates to surgical dental implant system made up of inert material with corrosion resistance and biocompatible nature, which are being capable of better osseointegration in the jawbone maxillae or mandible without any rejection and infection.

The present invention also relates to surgical dental implant system, which has unique combination of different advantages: Enhanced stability, esthetics, easy to handle, minimal inventory and cost effectiveness.

The present invention relates to a dental implant system having the property of enhanced stability due to maintenance of alveolar bone and improved biomechanics at the implant abutment interface.

The present invention relates to the method of making the screw shape dental implants with tapering sides in lower and middle portion of the implant (conical shape) and parallel sides in upper portion (cylindrical shape) to increase the surface area and for easy insertion during implantation in the drilled bone site.

Present invention provides screw dental implant with external surface incorporating self-tapping threads of specific shape, pitch, and depth in the lower, middle and upper portion except the crestal modular area of the implant for increasing surface area.

The invention describes about the unique combination of buttress shape threads on the body of the implant with cervical micro threads, which enhances the self tapping nature of the tapering screw implant, improves the biomechanics at the implant abutment interface, lowering shear stresses at the bone implant interface and favorably distributing the stresses at the crestal level of alveolar bone thus reducing the resorption of alveolar bone, resulting in enhanced stability and longer life of dental implant under function.

Present invention describes about the internal attachment of the screw type dental implant for the abutment, which directly sits on the implant with the help of abutment screw. The internal portion has upper part of leading bevel for easy seating of the abutment on the top portion of implant, middle part of the hexagonal chamber and the lower part of the long channel for tightening and stabilizing the abutment screw.

The present invention concerns with the dental implant system with multifunctional component for serving the purpose of implant mount for carrying the implant from sterilized container to the implant site, impression analog to make the negative replica of the implant and abutment, and final abutment for placing the prosthesis on the top.

The present invention concerns with the dental implant system is to preserve the alveolar bone support by incorporating the feature of internal and medialised implant abutment connection which keeps the implant abutment interface away from the crest of alveolar bone thus reducing the insult of crestal bone from bacterial contamination and micro movements at this interface.

Accordingly the invention provides a dental implant system (FIG. 1) for supporting a prosthetic device comprising following components in combination wherein the stress values generated by the implant on the bone lie within the physiological limits (1-60 MPa) of bone remodeling:

a) A dental implant fixture [FIG. 1(2)] having buttress threads [FIG. 2(15)] on the body along with microthreads [FIG. 2(14)] on the collar.

b) A dental multifunctional component [FIG. 1(3)] used as an implant mount, impression analog, and as final abutment.

c) an dental abutment screw [FIG. 1(4)] with long internal hex channel [FIG. 10(59)] in the head portion In an embodiment of the present invention the said Multifunctional component [FIG. 1(3)] has the distinctive features of single prosthetic platform for all implant diameters; medialised implant abutment junction; concave transmucosal profile for better esthetics; and an additional internal threaded portion for securing abutment screw.

In still another embodiment of the invention, the said implant fixture comprises of Upper part/coronal part/crestal module/first part [FIG. 2(5)] having cylindrical shape with parallel sides and constant diameter of 5-10% of the total length of implant fixture.

Middle part/intermediate section/second part [FIG. 2(7)] having cylindrical shape with paralleling sides and constant diameter ranging between 20-25% of the total length of implant fixture.

Lower part/apical part/third part [FIG. 2(8)] having conical shape with tapered sides and decreasing diameter apically ranging between 60-75% of the total length of implant fixture.

In yet another embodiment of the invention the said implant fixture has a length in the range of 8-15 mm and a maximum outer diameter of 3.5-6 mm.

In yet another embodiment of the invention the said implant fixture has crestal module of height 2-3 mm with top wide flat surface.

In yet another embodiment of the invention the said implant fixture has a crestal module of height 2-3 mm with surface treated non-threaded collar [FIG. 2(13)] of height ranging from 0.4 mm-0.8 mm.

In yet another embodiment of the invention the said implant fixture has a crestal module [FIG. 2(5)] with circumferential micro threads [FIG. 3(14)] of depth [FIG. 3(19)] in the range of 50-100 um, pitch [FIG. 3(20)] in the range of 100-150 um and covering 1.2 mm-1.6 mm height of crestal module.

In yet another embodiment of the invention the said implant fixture has a single lead threaded profile on middle and apical part thus covering 70%-90% area of the implant surface.

In yet another embodiment of the invention the said implant fixture has buttress threads [FIG. 2(15)] with upper surface [FIG. 3(21)] making an angle 80°-100° to the long axis of the implant and the lower bevel surface [FIG. 3(22)] having an obtuse angle of about 110°-135°.

In yet another embodiment of the present invention the said implant fixture has buttress threads with depth [FIG. 3(23)] in the range of about 0.275-0.375 mm and pitch [FIG. 3(24)] in the range of 0.5-0.85 mm and pitch surface in the range of 100-150 um.

In yet another embodiment of the invention, the said implant fixture has apical part [FIG. 2 (8)] consisting of apical end [FIG. 2 (17)] with rounded shape and longitudinal apical recess [FIG. 2(18)].

In yet another embodiment of the invention the said implant fixture has an internal portion [FIG. 4(26)] extending from the crestal module portion [FIG. 2(5)] upto the middle portion of the implant for connecting the implant with the abutment [FIG. 1(3)] and comprises of:
Leading internal bevel [FIG. 4(27)] at the angulation of 10-20 degrees;
Internal hexagonal shape chamber [FIG. 5(28)] with the height in the range of 1-2 mm;
Threaded channel [FIG. 5(29)] of about 2-3 mm.

In yet another embodiment of the invention the said multifunctional component is capable of functioning as:
implant mount to transfer the implant from the container to the bone site;
impression analog to make the negative replica of the implant and;
the final abutment to place the prosthesis.

In yet another embodiment of the invention the said multifunctional component has a length to diameter ratio of 3:2

In yet another embodiment of the invention the said multifunctional component has a single diameter and length for different diameters of implant fixture (single prosthetic platform).

In yet another embodiment of the invention the said multifunctional component has a diameter smaller than the implant top surface, thus medialising the implant-abutment junction.

In yet another embodiment of the present invention the said multifunctional component comprises of:
upper portion [FIG. 6(30)] which is 10-20% of the total length of multifunctional component;
middle portion [FIG. 6(31)] which is 60-70% of the total length of multifunctional component; and
lower portion [FIG. 6(32)] which is 20-30% of the total length of multifunctional component.

In yet another embodiment of the present invention the said multifunctional component has an upper portion consisting of square shaped head [FIG. 6(33)] for engaging the hand ratchet while screwing the implant fixture into the bone and perpendicular flange and the undercut surface [FIG. 6(35)] for the retention of the impression material.

In yet another embodiment of the invention the said multifunctional component has an upper portion which is cut during the final abutment from the multifunctional component.

In yet another embodiment of the present invention the said multifunctional component has a middle portion consisting of annular grooves [FIG. 6(39)] and horizontal lines which can serve as reference lines for ease in milling and preparing the multifunctional component as an abutment for reduction of height and preparation of finish line on abutment respectively.

In yet another embodiment of the invention the said multifunctional component has a middle portion [FIG. 6(31)] consisting of flat cut surface with the window shape design, the base which is parallel to one of the side of the hexagonal shaped internal chamber [(FIG. 5 (28)] of the implant fixture, thus determines the proper orientation of the multifunctional component to the buccal aspect of the implant In yet another embodiment of the invention the said multifunctional has lower portion consisting of concave transmucosal part [FIG. 6(45)] which gives an esthetical emergence profile to prosthesis placed over the abutment.

In yet another embodiment of the present invention the said multifunctional component has internal channel [FIG. 7(54)] of decreasing diameter of 3.5 mm to 1.85 mm from the upper portion, to middle portion and to lower portion.

In yet another embodiment of the invention the said multifunctional component has an additional threaded portion [FIG. 7(55)] in the lower part of the internal channel which helps in securing the abutment screw while getting it disengaged from the implant fixture internal channel.

In yet another embodiment of the present invention the said abutment screw has a length ranging from 11-19 mm when used with final abutment and impression coping and comprises of:
the upper head portion [FIG. 9(56)]—25% to 40% of the total length of the abutment screw;
middle shaft portion [FIG. 9(57)]—30% to 60% of the total length of the abutment screw; and
lower threaded portion [FIG. 9(58)]—15% to 30% of the total length of the abutment screw.

In yet another embodiment of the invention the said abutment screw has upper, middle and lower portions in the ratio of 25%:60%:15% respectively when the multifunctional component is to be used as an impression analog.

In yet another embodiment of the invention the said abutment screw has an internal portion with hexagonal channel [FIG. 10, 11(59)] with sides 0.70-0.80 mm and depth of 4-5 mm, which allows the reduction of the multifunctional component during fabrication of abutment to adjust in varied inter-ridge distances.

In yet another embodiment of the invention the said dental implant system yields stresses in the range of 18-39 MPa, at different locations (implant abutment junction, crestal area and cortico-cancelous junction) of the implant abutment assembly or implant system, under compression type of forces of 450N.

In yet another embodiment of the invention the said dental implant system yields stresses in the range of 18-39 MPa, at different locations (implant abutment junction, crestal area and cortico-cancelous junction) of the implant abutment assembly or implant system, under tension type of forces of 450N.

In yet another embodiment of the invention the said dental implant system is disposed within the mouth wherein the implant fixture is screwed into a bore-drilled into tooth less-site in a maxilla or mandible jaw bone, on which the multifunctional component is inserted and fixed by the abutment screw.

In yet another embodiment of the invention the stress values are calculated using Finite Element Analysis.

BRIEF DESCRIPTION OF DRAWINGS

In the drawing accompanying this specification.

FIG. 13 Shows the FEA model depicting the perspective view of the implant fixture with the different thread types viz. Buttress (a), Reverse buttress (b), Buttress with microthreads (c) and classical V shape (d) under tension type of forces.

FIG. 16 shows FEA model with the cross-section of the implant system and the surrounding bone.

FIG. 17 shows FEA model depicting the cross-section of the implant system with different thread design viz. classical V (a), buttress (b), reverse buttress (c) and buttress with microthreads (d) with the surrounding bone.

FIG. 22 FEA model of the implant system with different types of thread design viz. Reverse Buttress (a), Buttress (b), Buttress with microthreads (c) and Classical V (d) showing the Von misses stresses generated under tension type of forces.

FIG. 23 FEA model of the implant system with different types of thread design viz. Reverse Buttress (a), Buttress (b), Buttress with microthreads (c) and Classical V (d) showing the Von misses stresses generated under moment type of forces.

DETAILED DESCRIPTION OF THE INVENTION

The terminologies used here in above and to be used further in the description of the invention are merely to explain the embodiments of the dental implant and are not intended to limit the scope of the invention.

To state: the implant body is the part of the dental implant which is implanted in the drilled bore in jaw bone, the lower end/apical end/lower portion of the said implant body is the end which is directed towards the bone and upper end is the one which receives the abutment for crown attachment and remains aligned with the crest of the bone or to the gingival and so on. It is to be understood that each terminology used includes all equivalent terminologies, which operate in a similar manner to accomplish similar functions.

The present invention will be described in details with respect to the accompanying drawings when taken in conjunction with the detailed description thereof and these and other objects will be more apparent hereinafter.

In the accompanying figures of drawings there is shown various views of a dental implant system (1) consisting of dental implant fixture (2), abutment/multifunctional component (3) and abutment screw 4.

Figure 1:
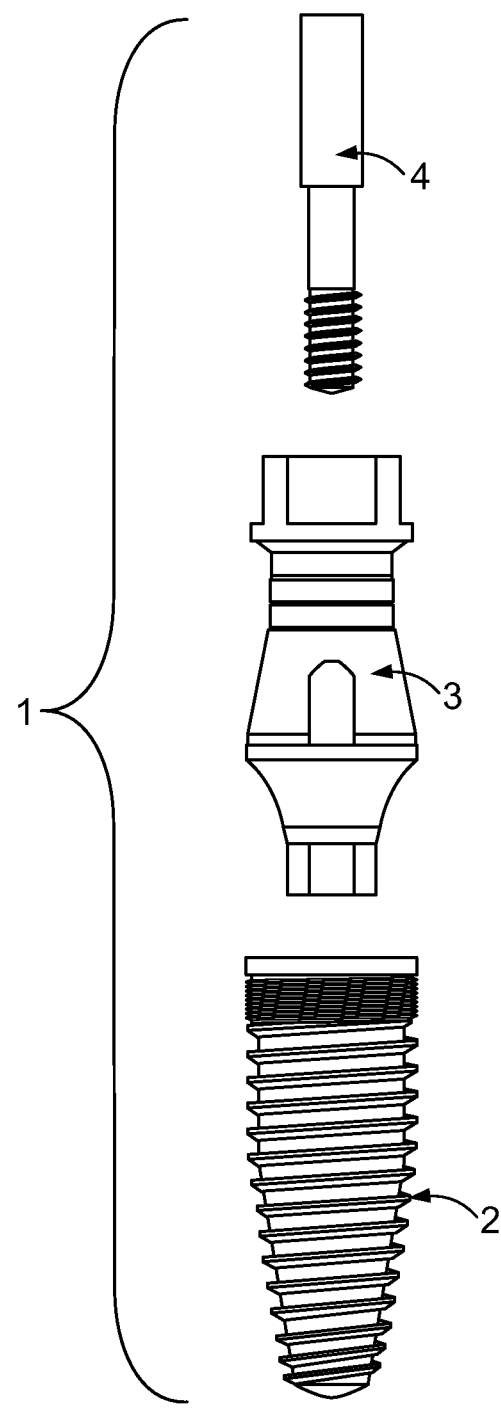
FIG. 1 is a side-perspective view of one embodiment of the dental implant system.

FIG. 1 shows the side view of the dental implant system (1) comprising an endosseous screw shape root form dental implant fixture (2) of circular cross-section and is made from Titanium alloy screwed into a bore-hole drilled into tooth less-site in a maxilla or mandible jaw bone, on which the multifunctional component (3) is inserted and fixed by the abutment screw (4).

Figure 2:
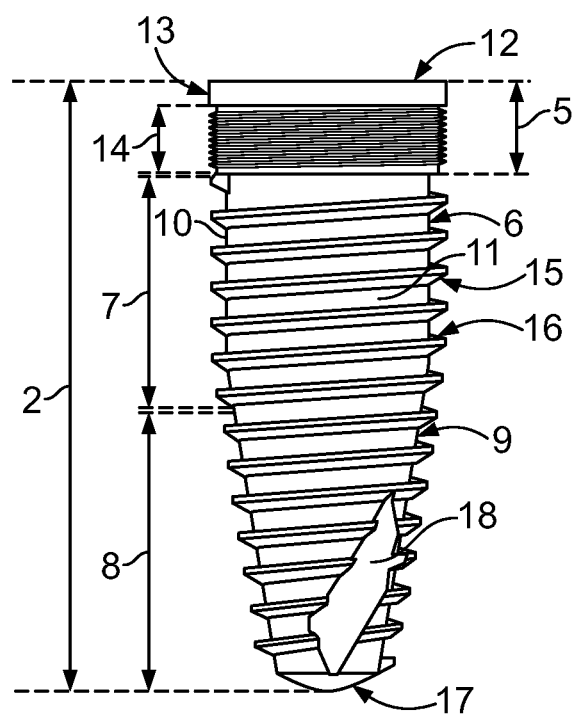
FIG. 2 is a side-perspective view of one embodiment of the dental implant fixture of this invention.

Referring to FIG. 2 the implant fixture (2) has an upper part/coronal end/crestal module/first part (5) which is cylindrical shape with parallel sides (6) of constant diameter, middle part/intermediate section/second part (7) having cylindrical shape with paralleling sides (6) of constant diameter, extending between first and third part and lower part/apical tapering part/third part (8) which is having conical shape with tapered sides (9) with decreasing diameter apically.

The implant fixture has a long axis (10) parallel to the three parts of the implant. The body of the implant (11) consists of the second part and third part of the implant fixture (2), has conical and cylindrical shape, which helps in easy insertion during implant fixture (2) placement and in acquiring the primary stability for better osseointegration respectively. The tapering structure also helps the implant fixture (2) in avoiding impingement on the anatomical structures.

The implant fixture (2) has a length in the range 8-15 mm depending on the clinical situation and a maximum outer diameter of 3.5-6 mm. The various combinations of length and diameter cover most of the anatomical variations of the alveolar bone for implant placement. The axial extent of the first part/crestal module (5) is 5-10% of the total length of the implant fixture (2), the axial extent of the second part/middle part (7) is 20-25% of the total length of the implant fixture (2) and the axial extent of the third part/apical part (8) is 60-75% of the total length of the implant (1). Thus the implant is made up of $2/3^{rd}$ lower conical part with tapering sides and $1/3^{rd}$ upper cylindrical part with parallel sides as a whole.

The first part/crestal module (5) of the implant has flat platform (12) on the top and consist of two portions, the surface treated non-threaded collar (13) and the roughened micro threaded area (14). The surface treated non-threaded collar (13) has paralleling sides (6) with rough surface and has length of 0.4-0.8 mm. This enhances better soft tissue and bone integration around the implant fixture (2). The micro threaded area (14) covers about 1.2-1.6 mm of the implant fixture (2) surface. This enhances the surface area of the crestal module (5) which favorably distributes the forces at the critical area of alveolar bone crest.

The cylindrical shape second part/middle part (7) starts from the crestal module (5), which has circumferential roughness due to screw thread profile. The screw thread profile is formed by single lead thread (15), which extends apically from the junction between the first and second sections. The tips of the screw threads (16) over the cylindrical intermediate section (7) all lie on common plane, which is parallel to the main long axis (10) of the implant fixture (2), and thus circumscribe the circumference of the cylindrical intermediate section (7). This gives the cylindrical intermediate section (7) its constant diameter.

The conical shaped apical part (8) starts from the second part coronally (7) and ends at the apical end (17). It has a screw thread profile, which is formed by single lead thread (15) design. The conical apical part has tapering sides (9), thus the implant body (11) does not have constant diameter in this portion. The tips of the screw threads (16) over the conical apical portion (8) all lie on common plane, which is not parallel to the main long axis (10) of the implant fixture (2).

There is a particular type of threads (15) in the intermediate (7) and apical portion (8) (implant body 11) of the implant fixture (2) thus covering more than ⅔ portion of the implant (2). This enhances the surface area of the implant fixture (2) and thus its osseointegration with the bone.

One of the preferred embodiments of the implant fixture (2) with tapering apical part (8) having rounded apical end (17) which prevents damage to vital structures even if the implant is placed in close vicinity or pressing against it. The embodiment also shows a vertical apical recess (18) which allows the collection of the bone chips as the implant is self-tapping and the borehole preparation is lesser than the diameter of the implant fixture (2).

Figure 3:
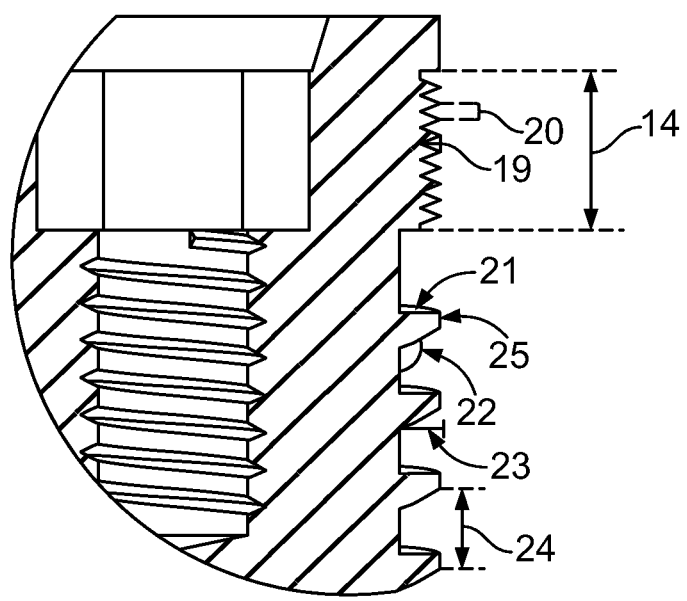
FIG. 3 is an enlarged, partial, cross-sectional view of one embodiment of the dental implant fixture of this invention.

FIG. 3 shows the magnified view of an implant fixture (2) embodiment, which describes the structure of micro threads on the crestal module and threads on the implant body. The implant fixture (2) has unique micro threads (14) with, thread depth (19) in the range of 50-100 um and pitch (20) in the range of 100-150 um.

The threads (15) have a buttress shape, with flat top surface and tapering lower surface. The top surface (21) makes 90° angulation with the long axis (10) of the implant fixture (2). The lower surface angulation (obtuse) (22) with the long axis (10) of the implant fixture (2) falls in the range of about 110°-135° degrees. Threads (15) have a depth (23) in the range of about 0.275-0.375 mm, pitch (24) in the range of 0.5-0.85 mm, and pitch surface (25) in the range of 100-150 um. Buttress threads (15) are incorporated in the implant fixture (2) to have self-tapping nature for easy insertion into the bone and better primary stability, while producing moderate amount of forces at the crest under different type of forces with comparable shearing component of the axial load at implant bone interface.

As in FIG. 2 and FIG. 3 the implant fixture (2) embodiment shows a unique combination of the buttress threads (15) on the implant body (11) i.e. more than ⅔rd part of the implant fixture (2) and micro threads (14) on the crestal module (5) of the implant fixture (2). This unique combination of the implant design has reduced stresses at the implant abutment interface and at the critical crestal level of alveolar bone and also it makes the implant fixture (2) of self-tapping nature. These findings have been substantiated by our FEA study done to compare the different types of threads (Buttress, V shape, reverse Buttress and Buttress with micro threads) under three types (compression, tension and moment) of forces.

Figure 4:
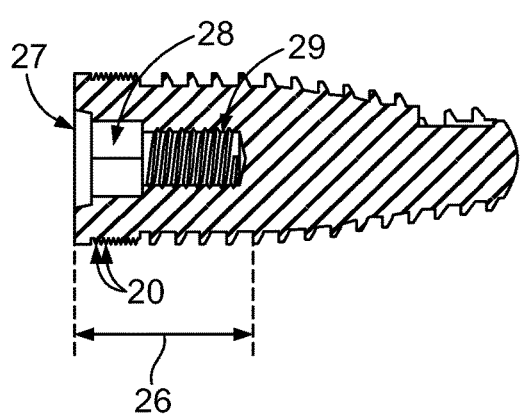
FIG. 4 is a side cut away view of the implant embodiment shown in FIG. 2, taken along line X-X in FIG. 5.

FIG. 4 shows one of the preferred longitudinal cross-sectional implant fixture (2) embodiments having the internal connection (26) for connecting the implant fixture (2) with the abutment (3). The internal connection (26) extends from the crestal module portion (5) of the implant fixture (2) upto the middle portion (7). The internal connection (26) has three sections, the leading internal bevel (27), internal hex chamber (28) and threaded channel (29). The leading internal bevel has an angulation with the long axis (10) of the implant fixture (2) in the range of 10-20 degrees for easy insertion of the abutment (3) into the implant fixture (2) and to have a better emergence profile for enhancing the overall esthetics of the prosthesis. The internal hex chamber (28) has a hexagonal shape with the height in the range of 1-2 mm. The threaded channel (29) allows proper seating and retention of the abutment screw and about 2-3 mm.

Figure 5:
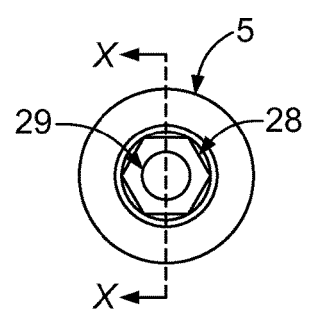
FIG. 5 is a top view of the implant embodiment shown in FIG. 2.

FIG. 5 shows the implant fixture (2) embodiment with the top plan view enumerating the flat top platform (12), the leading internal bevel (27) internal hex chamber (28) and threaded channel (29).

Figure 6:
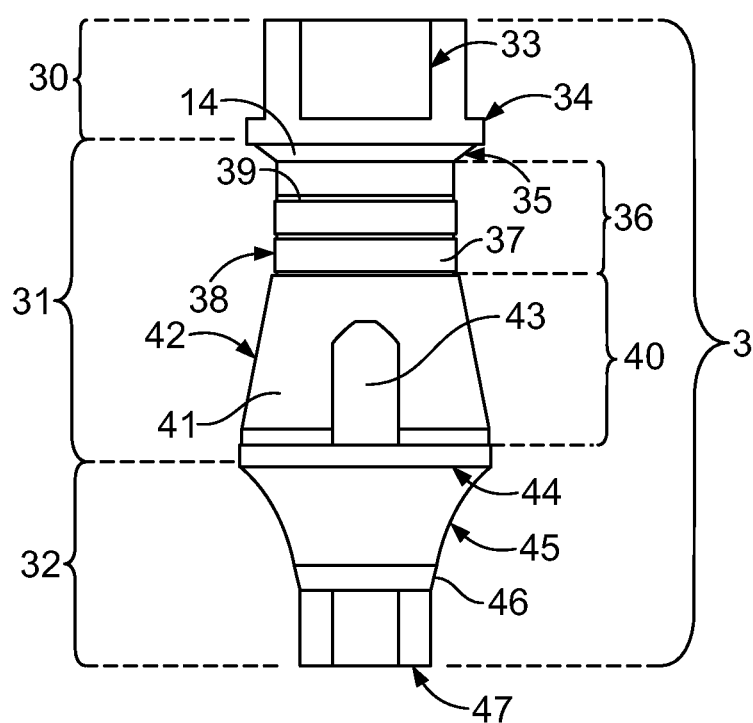
FIG. 6 is a side-perspective view of one embodiment of the multifunctional component.

FIG. 6 shows the multifunctional component (3) embodiments of the implant system (1) with the length to diameter ratio of 3:2. The multifunctional component (3) can function as implant mount to transfer the implant from the container to the bone site, impression analog make the negative replica of the implant and the abutment surface and final abutment for placing the prosthesis on the top. The multifunctional component (3) has single dimension for all the different diameters of the implant i.e. have a single prosthetic platform. The multifunctional component (3) has a diameter lesser than the top platform surface of the implant thus having the benefit of medialised implant abutment junction.

The multifunctional component (3) has three external parts upper portion (30) which is 10-20% of the total length, middle portion (31) which is 60-70% of the total length and the lower portion (32) which is 20-30% of the total length.

The upper portion (30) consist of square shape head (33) for engaging the hand ratchet while screwing the implant into, the bone prepared site, flange (34) perpendicular to the square head (33) and the undercut surface (35) for the retention of the impression material to the multifunctional component (3) while making the impression. The upper portion (30) is cut during the fabrication of final abutment from the multifunctional component (3).

The middle portion (31) comprises the main body of the multifunctional component (3) and starts at the undercut surface (35) of the upper portion (30). The top part (36) of the middle portion (31) consists of smooth surfaces (37) with parallel sides (38) divided by the three annular grooves (39). The annular grooves (39) give retention to the impression material while impression making. However the annular grooves (39) serve as reference lines for ease in milling and preparing the multifunctional component (3) as an abutment. This leads to reduction in the height of multifunctional component (3) to accommodate the prosthesis. The lower part (40) of the middle portion (31) consists of smooth surface (41) with the tapering sides (42) towards the top part (36). The smooth surface (41) has a flat cut surface (43) with the window shape design. The base (43) of the flat cut surface (43) is parallel to one of the side of the hexagonal shape internal chamber (28) of the implant fixture (2), thus determines the proper orientation of the multifunctional component to the buccal aspect of the implant (2). The lower part (40) of the middle portion (31) contains horizontal markings (44), which helps in preparation of finish line on abutment for the prosthesis placement.

The lower portions (32) of the multifunctional component (3) consist of the concave transmucosal part (45), which is surrounded by the soft tissues after the multifunctional component (3) is placed over the implant fixture (2). Transmucosal part (45) gives an esthetical emergence profile to prosthesis placed over the abutment. The lower portion (32) comprises the beveled surface (46) and the hexagonal chamber corresponding part (47) that fits to the leading internal bevel (27) and the hexagonal chamber (28) of the internal portion (26) of the implant fixture (2) respectively. They are the corresponding attaching parts of the internal type of connection between multifunctional component (3) and the implant fixture (2).

Figure 7:
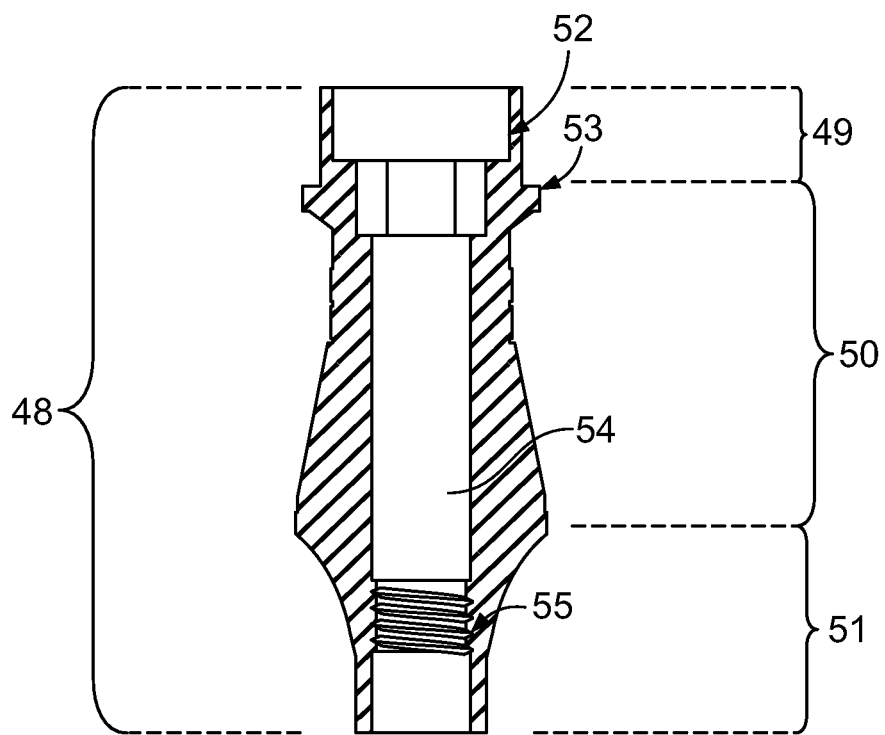
FIG. 7 is a side cut away of the multifunctional component embodiment shown in FIG. 6, taken along line X-X in FIG. 8.

FIG. 7 shows the longitudinal section of the internal portion (48) of the multifunctional component (3). The internal portion (48) is similarly divided into upper (49), middle (50) and lower portion (51) as the external surface of the multifunctional component (3). The upper portion (49) from the top consist of square shape wide opening (52) which helps in easy access for engagement of the abutment screw (4) and implant driver. The upper portion consists of hexagonal shape recess (53) for securing the implant driver. The middle portion (50) consists of internal channel (54) with circular shape for passing the abutment screw (4). The lower portion (51) also has internal channel (54) for passing the abutment screw (4) however, there is an additional threaded portion (55) which helps in securing the screw (4) and avoids its sudden fall from the multifunctional component after the screw (4) get disengaged from the implant (4) internal channel (29). In one of the preferred embodiments, the internal portion (48) of the multifunctional component (3) has a decreasing diameter of 3.5 mm to 1.85 mm from the upper portion (49) to lower portion (51).

Figure 8:
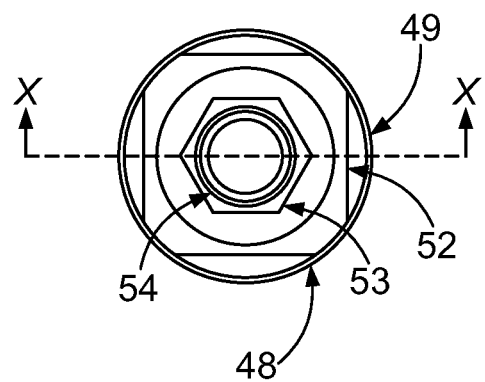
FIG. 8 is a top view of the multifunctional component shown in FIG. 6

FIG. 8 shows the multifunctional component (3) embodiment with the top plan view enumerating the external top surface of the upper portion (30), the internal portion (48) with upper portion (49), square shape wide opening (52), hexagonal shape recess (53) and the internal channel (54).

Figure 9:
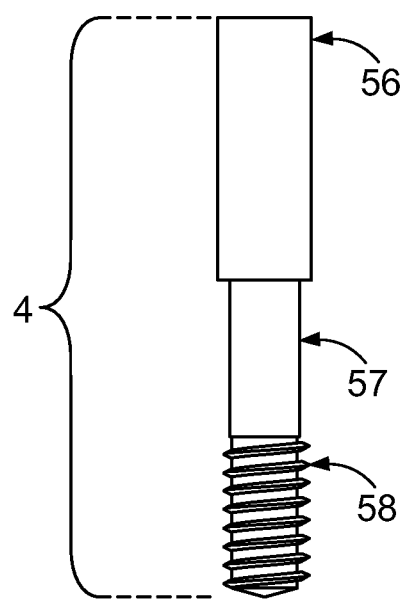
FIG. 9 is a side-perspective view of one embodiment of the abutment screw.

FIG. 9 shows the side view of abutment screw (4), ranging in length from 11-19 mm with three parts i.e. the upper head portion (56), middle shank portion (57), and lower threaded portion (58). The abutment screw have the upper portion (56) which is 40% of the total length, middle portion (57) which is 30% of the total length and the lower portion which is 30% of the total length. However, when the multifunctional component is used as impression analog a long screw is used in which the upper, middle and lower portions are in 25%, 60% and 15% respectively. The head (56) of the screw (4) is of hexagonal shape whereas the shank (57) and the threaded portion (58) are of circular shape. The threaded portion (58) of the screw (4) fits in the internal channel (29) of the implant (20).

Figure 10:
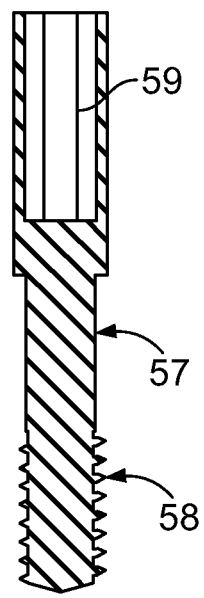
FIG. 10 is a side cut away view of the abutment screw embodiment shown in FIG. 9, taken along line X-X in FIG. 11.

FIG. 10 shows the longitudinal section of the internal portion (59) of the screw (4). The internal portion (59) has hexagonal shape with side 0.75 mm and depth of 4 mm, which allows the reduction of the multifunctional component during fabrication of abutment to adjust in varied inter-ridge distances.

Figure 11:
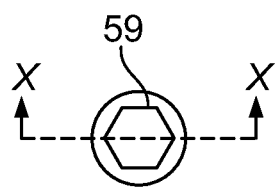
FIG. 11 is a top view of the abutment screw embodiment shown in FIG. 9.

FIG. 11 shows the multifunctional component/abutment screw (4) embodiment with the top plan view enumerating the hexagonal internal portion (59).

DISCLOSURE OF THE INVENTION

The upper portion of the external surface of implant is the region surrounded by the crest of bone. The mechanical stresses falling at the crest play a critical role in its resorption. Both the inadequate forces (no stimulating factor due to stress shielding effect) and excessive forces (shearing forces) lead to bone resorption. There are different types of crestal module of the implant depending upon the shape (cylindrical, tapered, reverse tapered), size (long, medium, short), and surface texture (smooth, polished, rough). However none have showed the ability of modulating the stresses at the crestal region, which can decrease the resorption of the bone. In the present invention microthreads are incorporated at the crestal module which enhances the roughened surface. This leads to effective mechanical loading of surrounding bone and reduction of the shearing stresses at the crestal level of alveolar bone. Thus better remodeling and preservation of alveolar bone takes place during function of implant.

In the present invention the unique combination of Buttress threads at the implant body with microthreads in the crestal module of particular dimensions are added to the implant design for
1) reducing the insertion stresses (self tapping) at the bone implant interface,
2) reducing the functional stresses at the alveolar crest bone,
3) reducing the stresses at implant abutment weak junction thus improving the biomechanics at the implant abutment interface.

Prior art has shown external and internal type of connection between implant and abutment. The internal portion of the implant has the chamber and the channel to secure the abutment and its screw. However in the present invention a leading internal bevel is introduced, which helps in easy insertion and alignment of the abutment with the implant.

Abutment is secured on the implant by the abutment screw, which passes through the internal channel of the abutment and fits into the implant internal channel. While removing the abutment from the implant screw has to be loosened carefully from the internal channel of the implant. However, in doing so, the screw can fall out from the abutment. Prior art shows no mechanism of securing the screw in the abutment after loosening from the implant channel. The present invention overcame this by introducing a threaded portion in the lower part of the abutment channel.

The abutment screw internally secures the implant abutment connection. The fabrication of the prosthesis on the abutment needs modification of the abutment height, width and shape. In the process of shortening the abutment height for the prosthesis accommodation, the abutment screw also gets reduced and loose its inner grooves required for tightening. However in the present invention the abutment screw head is of longer dimension, which have the grooves throughout its head length. Thus the tightening properties of the abutment screw can still be maintained even after the abutment and the screw is reduced for accommodating the prosthesis.

Dental implant system consists of many inventories like implant mount, impression analog, and implant analog and abutment for placing the prosthesis on the implant fixture. The present implant systems have separate abutment for each implant diameter size. This also increases the inventory and makes difficult for the operator in understanding and handling the implant system. However, the present invention introduces the multifunctional component in the dental implant system. The multifunctional component of the system serves the purpose of implant mount, impression analog and final abutment. In addition the multifunctional component is designed with single prosthetic platform so one component is compatible with different implant dimensions. Thus the multifunctional component minimses the inventory needed for the implant system and allows easy handling of the system.

The early bone loss at the crest of alveolar bone often lost to the first thread, after the loading of implants is a common clinical observation. This loss of bone is contributed by many factors. However one of the factors considered is the implant abutment interface. In the prior art the size of the implant platform coincides with the diameter of the abutment. This type of implant and abutment interface is broader and near to the crest of bone thus resulting in faster bone loss due to bacterial contamination and micromovement at the interface (microgap). In the present invention the implant abutment interface is medialised (radially inward) by using smaller diameter abutment on the bigger implant platform, which keeps the interface away from the crest of alveolar bone, thus reducing the insult of crestal bone from bacterial contamination and micro movements.

Esthetics is an important aspect in designing the abutment of implant system. The shape of the abutment determines the emergence profile of the prosthesis placed on the implant fixture. There are various shapes of the transmucosal portion of the abutment like cylindrical, oblong, convex etc. However these shapes of the abutment don't provide an esthetical emergence profile to the prosthesis. Thus to overcome this, the present invention developed a concave shape of the lower transmucosal part of the abutment to have an better emergence profile of the prosthesis placed on the abutment simulating the natural tooth anatomy.

Current implant systems available, apart from the high cost of equipment and the fixtures, offer a wide gamut of prosthetic options, which requires a high input for inventory management and complicates the treatment planning. This is a major factor due to which this treatment option is yet to reach the masses. Hence there is a need to develop a new convenient and economical dental implant system that has more universal and streamlined numbers of components without compromising the basic tenets of implant design.

A better understanding of the present invention is provided by the following examples which is set forth to illustrate, but is not to be construed to limit, the present invention.

Example 1

Finite Element Study in Support of the Present Invention

Finite Element Analysis (FEA) is a computer based numerical technique for solving wide range of engineering problems. It can be used to calculate deflection, stress, strain, vibration response, buckling behavior and many other phenomena. It can also used to analyze wide range of material models such as isotropic, orthotropic, anisotropic etc., FEA is be used to simulate the wide range of material response such as linear/non-linear response, elastic and plastic deformation and also time independent/dependent material responses. The computer is required because of the considerable number of numerical calculations required to analyze the structure behavior for the given external loads. A mesh is needed in FEA to divide the whole domain into elements.

Discretization of a Domain

It is the process of creating a mesh, elements and their respective notes and defining boundary conditions. In the Finite Element method, a structure is discretized into many small simple blocks or elements. The behavior of the each element can be described using a relatively simple set of equations. Just as a set of elements can be joined together to build a whole structure, likewise the equations describing the behavior of individual elements are joined into an extremely large set of equations that describe the behavior of the whole structure. From the solution, the computer extracts the behavior of individual elements. From this it can calculate the stress and deflection of all the parts of the structure.

Derivation of Element Equations

Finite Element (FE) model generated as a solid model with the solid element mesh of individual elements and perform the pre-process, solution and post processing to calculate the stresses and strains.

The study of solid mechanics is concerned with the equations of the equilibrium, strain-displacements relations and the constitutive law. It is well known that the assumption of the strains being infinitesimal leads to a linear analysis, while the use of generalized Hooke's law between stress and strain give rise to a linear elastic-plastic analysis, viscoelastic or viscoplastic models can be incorporated by using appropriate constitutive modeling. Retaining the higher order terms in strain displacement relations can simulate geometric nonlinear effects in solid mechanics.

For linear elastic analysis, the FEA program sets up stiffness matrix and load vector and then solves for displacement vector at equilibrium position, thereby producing displacement results for each node. These displacements will then be used to calculate strains and these strains are further used to calculate stress using Hook's law.

Stress and strain relation of a linearly elastic and isotropic material is given by:

$$\begin{Bmatrix} \varepsilon_x \\ \varepsilon_y \\ \gamma_{xy} \end{Bmatrix} = \begin{bmatrix} \frac{1}{E} & \frac{-\upsilon}{E} & 0 \\ \frac{-\upsilon}{E} & \frac{1}{E} & 0 \\ 0 & 0 & \frac{1}{G} \end{bmatrix} \begin{Bmatrix} \sigma_x \\ \sigma_y \\ \tau_{xy} \end{Bmatrix} + \begin{Bmatrix} \varepsilon_{x0} \\ \varepsilon_{y0} \\ \gamma_{xy0} \end{Bmatrix}$$

where $\varepsilon_x$ and $\varepsilon_y$ are normal strains in x and y directions respectively, $\upsilon_{xy}$ is the shear strain in x-y plane, $\sigma_x$ and $\sigma_y$ are normal stresses in x and y directions respectively, $\tau_{xy}$ is shear stress in x-y plane, E is the elastic modulus, '$\upsilon$' is Poisson's ratio, and 'G' is the shear modulus, $G=E/(1+\upsilon)$. The last column vector contains initial strains (described below). Abbreviated, equation is written as:

$$\ldots \gamma\sigma + \epsilon_0$$

This equation is solved for the stress vector $\sigma$, we have $$\ldots \gamma\epsilon_0 + \sigma_0$$

in which $\sigma_0 = -\epsilon_0$

Equation for Plane Stress and Plain Strain Under Mechanical Load $$\begin{Bmatrix} \sigma_x \\ \sigma_y \\ \tau_{xy} \end{Bmatrix} = \frac{E}{1-\upsilon^2} \begin{bmatrix} 1 & \upsilon & 0 \\ \upsilon & 1 & 0 \\ 0 & 0 & \frac{1-\upsilon}{2} \end{bmatrix} \begin{Bmatrix} \varepsilon_x \\ \varepsilon_y \\ \gamma_{xy} \end{Bmatrix} \text{ for plane stress}$$

$$\begin{Bmatrix} \sigma_x \\ \sigma_y \\ \tau_{xy} \end{Bmatrix} = \frac{E}{(1+\upsilon)(1-2\upsilon)} \begin{bmatrix} 1-\upsilon & \upsilon & 0 \\ \upsilon & 1-\upsilon & 0 \\ 0 & 0 & \frac{1-2\upsilon}{2} \end{bmatrix} \begin{Bmatrix} \varepsilon_x \\ \varepsilon_y \\ \gamma_{xy} \end{Bmatrix} \text{ for plane strain}$$

Equation for Plane Stress and Plain Strain Under Thermal Load $$\varepsilon_0 = \begin{Bmatrix} \alpha \Delta T \\ \alpha \Delta T \\ 0 \end{Bmatrix} \text{ for plane stress}$$

$$\varepsilon_0 = \begin{Bmatrix} \alpha \Delta T \\ \alpha \Delta T \\ 0 \end{Bmatrix} (1+\upsilon) \text{ for plane strain}$$

$$\varepsilon_x = \frac{\partial u}{\partial x}$$

$$\varepsilon_y = \frac{\partial v}{\partial y}$$

$$\gamma_{xy} = \frac{\partial u}{\partial x} + \frac{\partial v}{\partial y}$$

$$\begin{Bmatrix} \varepsilon_x \\ \varepsilon_y \\ \gamma_{xy} \end{Bmatrix} = \begin{bmatrix} \frac{\partial}{\partial x} & 0 \\ 0 & \frac{\partial}{\partial y} \\ \frac{\partial}{\partial y} & \frac{\partial}{\partial x} \end{bmatrix} \begin{Bmatrix} u \\ v \end{Bmatrix}$$

where 'u' and 'v' are the nodal displacements in 'x' and 'y' direction respectively.

$$\begin{Bmatrix} u \\ v \end{Bmatrix} = \begin{bmatrix} N_1 & 0 & N_2 & 0 \\ 0 & N_1 & 0 & N_2 \end{bmatrix} \begin{Bmatrix} u_1 \\ v_1 \\ u_2 \\ v_2 \end{Bmatrix}$$

or $u = Nd$ where '$N_i$' is separate shape polynomials and 'N' is the shape function matrix
where i=1, 2, 3, 4 . . .
$\epsilon = Bd$, and $\sigma = EBd$
where, 'B' is called as strain-displacement matrix.

The potential energy (Π) of an elastic body is defined as sum of total strain energy (U) and the work potential (WP) and is given as:

$$\Pi = U + WP$$

where 'U' is the strain energy and 'WP' is the work potential $$U = \frac{1}{2} \int_e \sigma^T \varepsilon dV$$

$$WP = -\int_e u^T f dV - \int_e u^T T ds - \sum_i u_i^T P_i$$

Assembly of element equations, element equations is assembled and boundary equations are introduced. Equations are computed by using Gaussian Elimination technique.

Finally, equations are solved for displacements at nodal points and strains/stresses are calculated from the stress 'B' Matrix. Matrix symbolization for the set of equations is given where 'K' is Global stiffness matrix derived from element stiffness
'R' is the Global load vector
'D' is the Global displacement at nodes
Equation for the stress is given by Hook's law as;

$$E = \sigma/\epsilon, \text{ or } \sigma = \epsilon E$$

Assumptions Made for Simplification of Bone Implants Characteristics

The difficulty in mechanical characterization of bone due to its complex structure and its interaction with the implant systems has led the investigators to make certain major simplifications. Contrary to the earlier studies where the trabecular pattern of the bone was ignored due to the lack of understanding of the trabecular pattern, most of the investigators have reached a consensus that the cortical bone is neither homogenous nor isotropic. However for the sake of ease of calculation in FE analysis without oversimplifying the bone structure, the bone is considered as transversely isotropic. Therefore, there exist different values for ultimate strain and modulus of elasticity when bone is tested in compression as compared within tension.

Material & Methods
Model Design

A computer aided design (CAD) of Two-Dimensional and Three-Dimensional solid model of a single osseointegrated implant with straight abutment in a segment of bone was generated. We used the ABAQUS V6.5 Finite Element analysis programmed to generate the solid model, create the mesh of individual elements and perform the post processing to calculate the stresses and strains. In the model titanium implants were designed using tapered shape, threaded design, and 1 mm coronal collar. Straight abutment of 9 mm height, square head with taper was screwed on the implant. Bone was modeled as a cancellous core/soft core surrounded by 2 mm of cortical/hard bone. Implant was opposed by cortical bone in crestal region (collar & threaded portion) where as the cancellous bone opposes remainder of threaded implant body surface.

Material Properties

All materials used in the models were considered to be isotropic, homogenous and linearly elastic. We modeled cortical and cancellous bone as homogenous material with transverse isotropy. A transversely isotropic material behaves identically in all planes perpendicular to the axis of symmetry. In our transversely base model, the axis of symmetry for bone, is in the mesodistal direction (Sagittal section).

The elastic properties used were taken from the literature:

Elastic Properties Ascribed to Materials Used In the Models

| Material name | Young's/Shear Modulus (GPa) | Poisson's ratio |
|---|---|---|
| Cortical bone | $E_1 = 126.0$; $E_2 = 19.4$; $E_3 = 12.6$, $G_{12} = 4.85$; $G_{13} = 4.85$; $G_{23} = 5.7$ | $\upsilon_{12} = 0.055$ $\upsilon_{13} = 0.322$ $\upsilon_{23} = 0.01$ |
| Cancellous bone | $E_1 = 114.8$; $E_2 = 21.0$; $E_3 = 1.148$, $G_{12} = 0.068$; $G_{13} = 0.068$; $G_{23} = 0.434$ | $\upsilon_{12} = 0.3$ $\upsilon_{13} = 0.253$ $\upsilon_{23} = 0.253$ |
| Titanium | $E = 110$ | $\upsilon = 0.3$ |

Interface Condition: We assumed complete or 100% osseointegration at the implant/bone interface and we modeled the restoration and abutment as a seamless/continuous unit.

Elements and Nodes: Models were meshed with 4-node solid linear tetrahedron elements (C3D4). A finer mesh was generated at the material interface to ensure accuracy of force transfer. The number of elements and nodes in each model is taken as an average i.e. elements 1, 38,121 and nodes 29,877.

Constraints and Forces: Models were constrained in all directions and on inferior border of bone at the nodes. The magnitude of force remained constant i.e. 450 N in each model however the direction of forces were changed.

Solution: Analysis for each model was performed by means of ABAQUS V6.5 software programme. The calculation time (average) for each model was about 2 hrs. The von Mises Stresses was used to display the stresses in the implant system and bone.

From the results of the FEA with regards to the thread designs under a load of 450 N the following data was extrapolated.

Comparing Buttress, Reverse Buttress, and V-Shape Thread Designs
  Under Compression
    At the abutment implant interface the maximum stress (on the implant) was seen in the Classical V (41.4 MPa), followed by reverse buttress (36.51 MPa), and with the least in Buttress (30.94 MPa).
    At the crestal level maximum stress was seen in Buttress (27.15 MPa), followed by Classical V (18.34 MPa), and with the least in Reverse Buttress (11.94 MPa).
    At the Cortico cancellous interface maximum stress was seen in Buttress (85.33 MPa), followed by Classical V (30.44 MPa), and with the least in Reverse Buttress (24.39 MPa).
  Under Tension
    At the abutment implant interface the maximum stress was seen in the Classical V (40.7 MPa), followed by Reverse buttress (37.57 MPa), and with the least in Buttress (33.95 MPa).
    At the crestal level maximum stress was seen in Reverse Buttress (44.38 MPa), followed by Buttress (27.15 MPa), and with the least in Classical V (18.34 MPa).
    At the Cortico cancellous interface maximum stress was seen in Buttress (85.33 MPa), followed by Reverse Buttress (63.34 MPa), and with the least in Classical V (30.99 MPa).
  Under Moment
    At the abutment implant interface the maximum stress was seen in the Classical V (425.34 MPa), followed by Reverse buttress (421.62 MPa), and with the least in Buttress (278.94 MPa).
    At the crestal level maximum stress was seen in Classical V (227.03 MPa), followed by Buttress (139.97 MPa), and with the least in Reverse Buttress (120.68 MPa).
    At the Cortico cancellous interface maximum stress was seen in Buttress (30.39 MPa), followed by Classical V (9.59 MPa), and with the least in Reverse Buttress (9.18 MPa).

Comparing Buttress with Microthreads and Buttress Thread Designs

To improvise upon the Buttress design, microthreads were added on the collar of implant. The comparison of Buttress with microthread design against Buttress design was done
  Under Compression
    At the abutment implant interface the Buttress with microthread showed slightly higher stresses (38.49 MPa), as compared to Buttress (30.94 MPa).
    At the crestal level Buttress with microthreads showed less stresses (18.48 MPa) as against Buttress (27.15 MPa).
    At the Cortico cancellous interface less stress were seen in Buttress with microthreads (18.15 MPa) as compared to Buttress (85.33 MPa).
  Under Tension
    At the abutment implant interface the Buttress with microthreads showed slightly higher stress (38.44 MPa) as compared to Buttress (33.95 MPa).
    At the crestal level Buttress with microthreads showed lesser stresses (18.48 MPa) than Buttress (27.15 MPa).
    At the Cortico cancellous interface Buttress with microthread (22.29 MPa) showed lesser stress than Buttress (85.33 MPa).
  Under Moment
    At the abutment implant interface the Buttress with microthreads showed higher stress (3968.09 MPa) as compared to Buttress (278.94 MPa).
    At the crestal level Buttress with micro threads showed lesser stresses (70.27 MPa) than Buttress (139.97 MPa).
    At the Cortico cancellous interface Buttress with micro thread (8.57 MPa) showed lesser stress than buttress (30.39 MPa).

Inference

From the above comparison made between the different thread designs under compression, tension and moment it was deduced that:
a. Buttress thread design was least detrimental in terms of the von Mises stresses generated at the implant abutment interface. Maximum number of failures takes place at the implant abutment interface, therefore to reduce the stresses at this interface, Buttress design is best suited. Moreover there is a better self-tapping nature of Buttress design, which further reinforces our selection.
b. Incorporation of micro threads into the collar of the implant with buttress design led to a dramatic reduction of stress in the bone at both the crestal and cancellous level.
c. Further the comparison of buttress with micro thread design against all other thread design (Classical V and Reverse Buttress), as seen in FEA models showed wider and more even distribution of von Mises stresses under compression, tension and moment forces.

Example 2

Figures 12A, 12B, 12C, 12D:
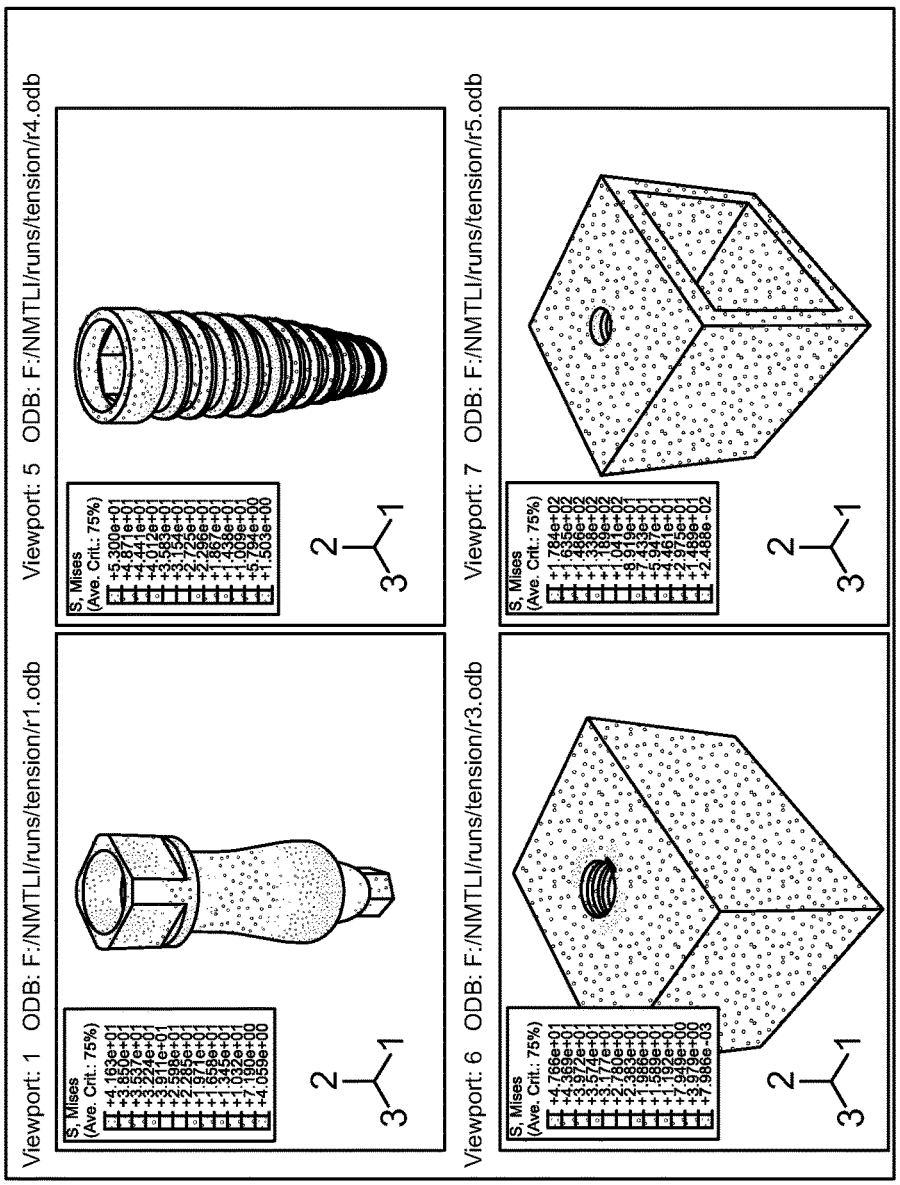
FIG. 12 shows the FEA models of the implant system components viz. Abutment (a) and Implant (b) and the surrounding Cancellous (c) and Cortical bone (d) under tension type of forces.

Initially an FEA model (FIG. 12) was created for the individual parts of the implant system (implant fixture and multifunctional component/abutment) and the cortical/cancellous bone surrounding the implant system. A tension force of 450 N was applied individually on the abutment/multifunctional component, implant fixture, cortical bone, and the cancellous bone.

After the analysis of the FEA model, the von misses stresses generated in the abutment at the top portion are in the range of 10-38 MPa, at the middle portion in the range of 4-29 MPa and at the lower, portion in the range of 13-32 MPa.

After the analysis of the FEA model, the von misses stresses generated in the implant fixture on the external surface at the crestal module are in the range of 10-48 MPa, in the middle threaded portion in the range of 5-22 MPa, and in the apical area in the range of 1.5-10 MPa. The internal portion of the implant fixture generated 10-35 MPa of stresses where as the top platform has the stresses in the range of 14-44 MPa.

After the analysis of the FEA model, the von misses stresses generated in the cortical bone at crestal level are in the range of 14-44 MPa.

After the analysis of the FEA model, the von misses stresses generated in the cancellous bone at crestal level are in the range of 3-31 MPa.

Example 3

An FEA model was generated to determine the stresses developed in the implant fixture having different types of threads i.e. Buttress, Reverse buttress, Buttress with microthreads and V shape under 450N of tensile type of load/forces. The FEA model shows the perspective view of the implant fixture under tensile forces.

In the FEA model of the implant fixture with the Buttress threads FIG. 13(a) when the 450 N of tensile force is applied, the external surface of the implant shows variable values of von misses stress in the range of 0.29-48.13 MPa. The crestal module/upper part of the implant exhibit stresses in the range of 5.61-16.24 MPa, the middle threaded portion exhibit forces in the range of 0.29-48.13 MPa, and the lower threaded portion exhibit the forces in the range of 0.29-5.61 MPa. The model shows that the von misses stresses are uniformly distributed and the highest stresses are in the body portion of the implant fixture, thus the implant fixture can withstand the 450 N forces better without any destruction.

In the FEA model of the implant fixture with the Reverse Buttress threads FIG. 13(b) when 450 N of tensile force is applied, the external surface of the implant shows variable values of von misses stress in the range of 1.5-35.18 MPa. The crestal module/upper part of the implant exhibit stresses in the range of 5.79-35.18 MPa, the middle threaded portion exhibit forces in the range of 1.5-35.18 MPa, and the lower/apical threaded portion exhibit the forces in the range of 0.299-5 MPa. The FEA model shows that the von misses stresses are uniformly distributed but the crestal module and the body portion exhibit the highest forces.

In the FEA model of the implant fixture with the Buttress threads and microthreads [FIG. 13(c)] when 450 N of tensile force is applied, the external surface of the implant shows variable values of von misses stress in the range of 0.936-13.8 MPa. The crestal module/upper part of the implant with microthreads exhibit the highest stresses in the range of 5.2-13.8 MPa, the middle threaded portion exhibit the forces in the range of 0.9-9.5 MPa, and the lower threaded portion exhibit the forces in the lowest range of 0.299-5 MPa. The FEA model shows the lowest and uniform type of stresses are generated in the implant fixture, with the highest stresses in the middle portion In the FEA model of the implant fixture with the Classical V shape threads [FIG. 13(d)] when 450 N of tensile force is applied, the external surface of the implant shows variable values of von misses stress in the range of 0.89-30.99 MPa. The crestal module/upper part of the implant exhibit stresses in the range of 8.41-30.99 MPa, the middle threaded portion exhibit forces in the range of 0.89-15.9 MPa, and the lower threaded portion exhibit the forces in the range of 0.89-8.41 MPa. The FEA model shows that the von misses stresses are not uniformly distributed and the crestal module exhibit the highest forces.

The comparison of FEA model of the implant fixture with the different thread design shows that the Buttress threads with microthreads shows the most uniform and the lowest amount of von misses stresses. Buttress thread design shows the lowest amount of stresses at the crest when compared to reverse buttress and classical V design. When microthreads are added to the buttress thread design the stresses at the crestal module become even lesser. Thus another advantage of this design is the lowest amount of stresses at the crestal module, which is the most prone area of the failure of implant (due to fracture or crestal bone loss).

Figure 14:
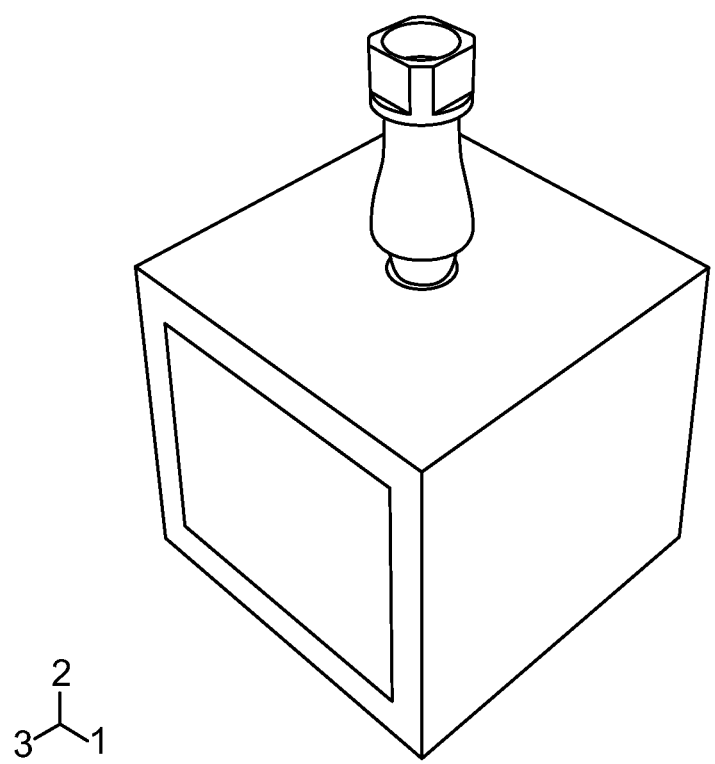
FIG. 14 shows FEA model of the integrated implant system with the surrounding bone.
Figure 15:
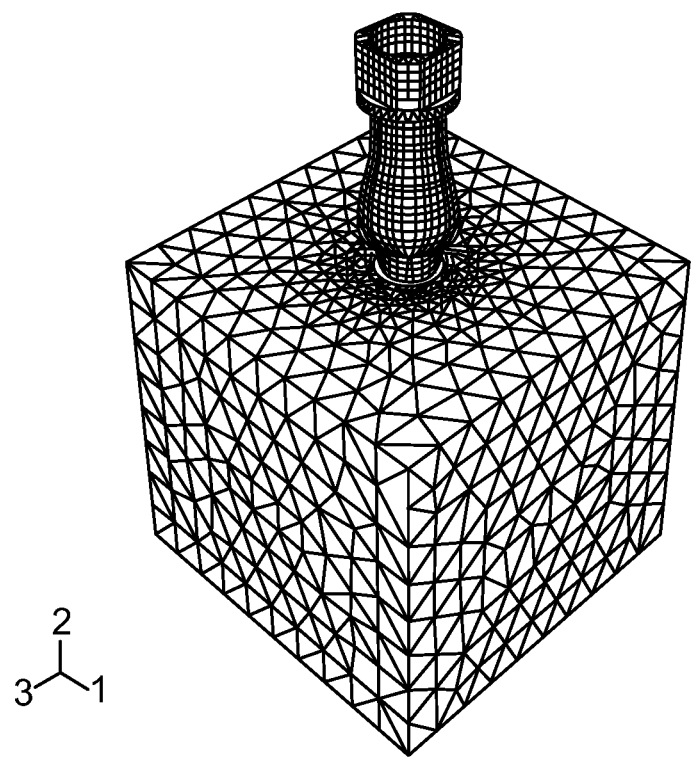
FIG. 15 shows FEA model with the mesh pattern of the implant system and the surrounding bone

After the initial FEA analysis consisting of the different components of the implant system, surrounding bone and implant fixture with the different thread shapes, an FEA model of the complete implant system (including implant fixture and multifunctional component) with the surrounding cortical and cancellous bone. At first a raw model was designed (FIG. 14) and later a meshed version (FIG. 15) was constructed with various nodes. At each node strain and stress can be calculated by using the FEA analysis equations (Hook's law) under different types of loads.

Thereafter an FEA model (FIG. 16) was generated showing the cross-section of the implant system with the surrounding bone. In this model a complete association between the internal connection of the implant and the multifunctional component is generated.

Later the FEA model (FIG. 17) of the cross-sectional view was made for implant system and surrounding bone with different thread types (Buttress, Reverse Buttress, Classical V and Buttress with microthreads).

Example 4

The FEA model generated for the complete implant system (including implant fixture with the buttress threads and multifunctional component) with the surrounding cortical and cancellous bone was used for evaluating the effect of compression type of force of about 450 N on the smallest (diameter 3.5 and length 10 mm) and the largest dimension (diameter 5 mm and length 13 mm) of the implant fixture included in the implant system. The evaluation was based on the magnitude and location of von misses stresses at different levels of the implant fixture having the Buttress thread design.

Figures 18A, 18B:
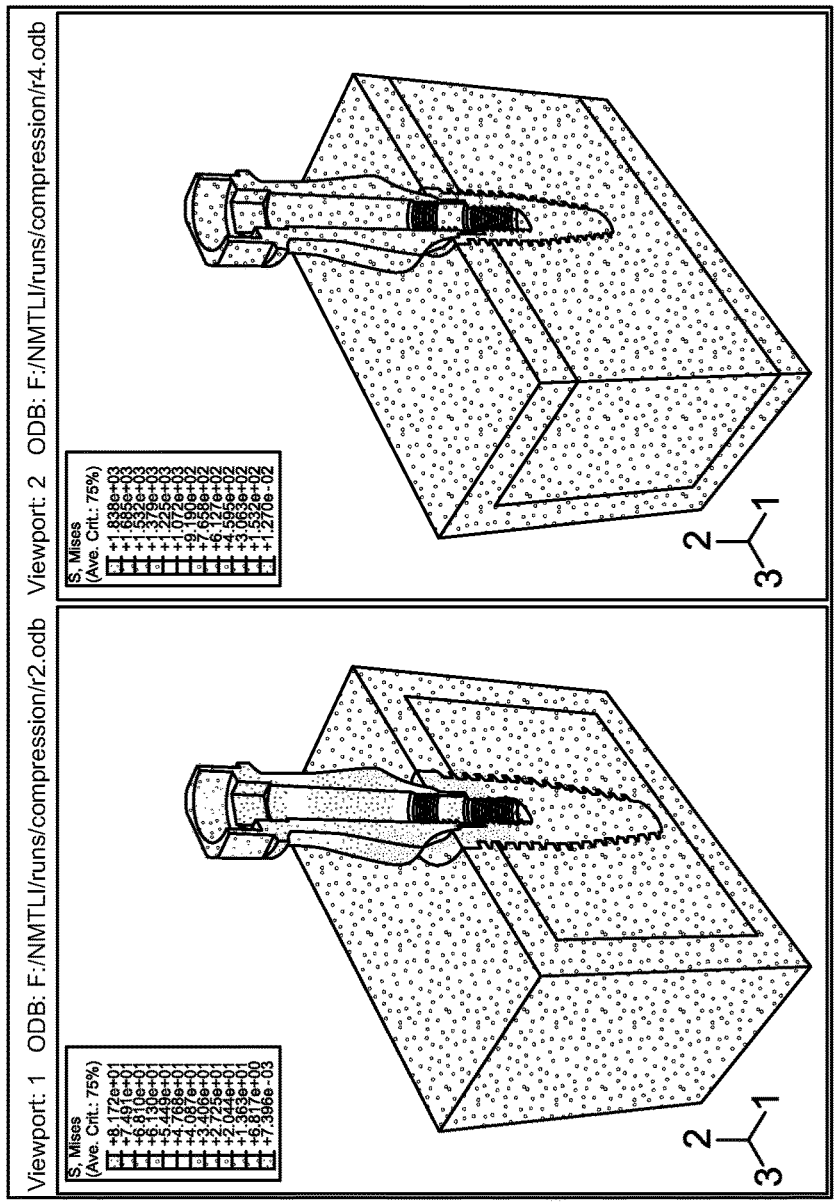
FIG. 18 shows the FEA model of the largest (a) and the smallest dimensions (b) of the implant system with buttress threads under compression type of forces.

In the FEA model, the implant system of the smallest [FIG. 18(b)] and the largest dimension [FIG. 18(a)] was evaluated for the von misses stresses under compression type of forces (450 N). When the compression force was applied on the implant system of largest dimension [FIG. 18(a)] the von misses stresses at implant abutment junction was recorded as maximum of 36.51 MPa, at the crestal bone level recorded as 11.94 MPa and at corticocancellous interface as 22.59 MPa. When the compression force was applied on the implant system of smallest dimension [FIG. 18(b)] the von misses stresses at implant abutment junction was recorded as 30.94 MPa, at the crestal bone level recorded as 27.15 MPa and at corticocancellous interface as 25.33 MPa. In comparison the largest dimension implant has higher von misses stresses at the implant abutment junction, whereas in smallest dimension implant corticocancellous interface has the higher stresses. The von misses stresses generated under compression forces mainly concentrate on the upper portion of the implant system and goes on decreasing in the apical direction.

Example 5

The FEA model generated for the complete implant system (including implant fixture with the buttress threads and multifunctional component) with the surrounding cortical and cancellous bone was used for evaluating the effect of tension type of force of about 450 N on the smallest (diameter 3.5 and length 10 mm) and the largest dimension (diameter 5 mm and length 13 mm) of the implant fixture included in the implant system. The evaluation was based on the magnitude and location of von misses stresses at different levels of the implant fixture having the Buttress thread design.

Figures 19A, 19B:
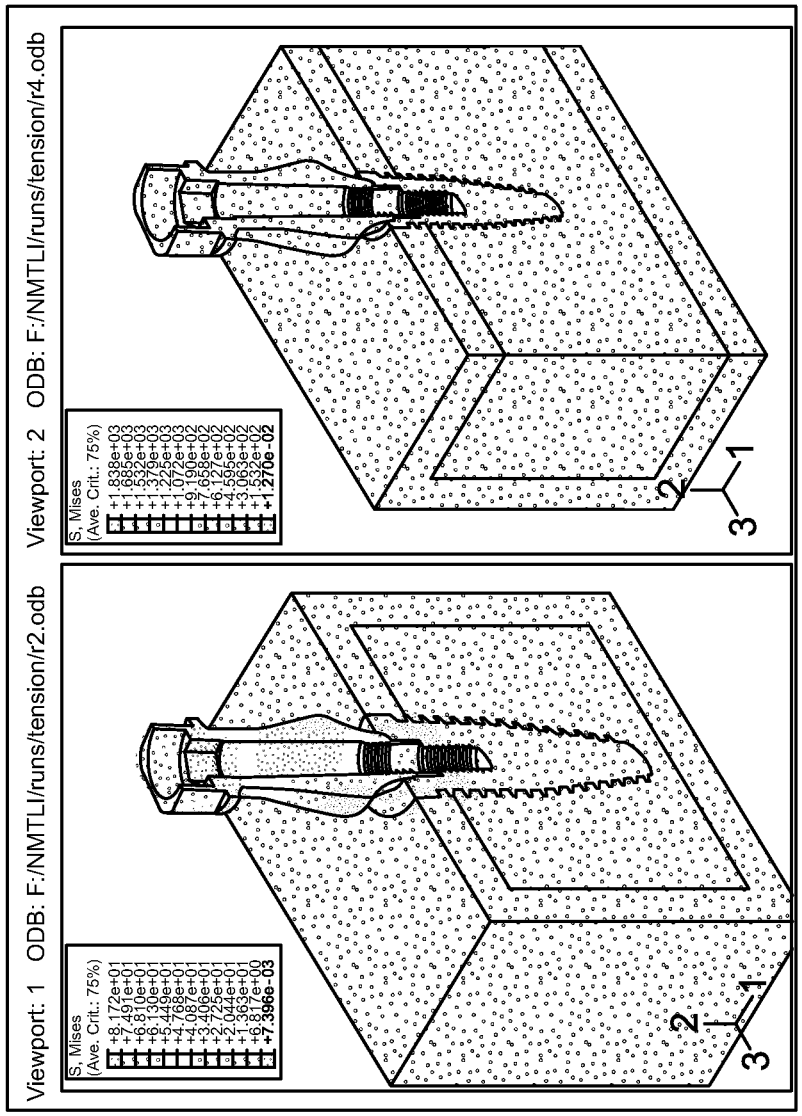
FIG. 19 shows the FEA model of the largest (a) and the smallest dimensions (b) of the implant system with buttress threads under tension type of forces.

In the FEA model, the implant system of the smallest [FIG. 19(b)] and the largest dimension [FIG. 19(a)] was evaluated for the von misses stresses under tension type of forces (450N). When the tension force was applied on the implant system of largest dimension [FIG. 19(a)] the von misses stresses at implant abutment junction was recorded as maximum of 36.59 MPa, at the crestal bone level recorded as 22.51 MPa and at corticocancellous interface as 22.59 MPa. When the compression force was applied on the implant system of smallest dimension [FIG. 19 (b)] the von misses stresses at implant abutment junction was recorded as 33.95 MPa, at the crestal bone level recorded as 27.15 MPa and at corticocancellous interface as 25.33 MPa.

In comparison the largest dimension implant has uniform stresses but higher von misses stresses at the implant abutment junction, whereas in smallest dimension implant corticocancellous interface has the higher stresses. The von misses stresses generated under tension forces mainly concentrate on the upper portion of the implant system and goes on decreasing in the apical direction.

Example 6

The FEA model generated for the complete implant system (including implant fixture with the buttress threads and multifunctional component) with the surrounding cortical and cancellous bone was used for evaluating the effect of moment type of force of about 450 N on the smallest (diameter 3.5 and length 10 mm) and the largest dimension (diameter 5 mm and length 13 mm) of the implant fixture included in the implant system. The evaluation was based on the magnitude and location of von misses stresses at different levels of the implant fixture having the Buttress thread design.

Figures 20A, 20B:
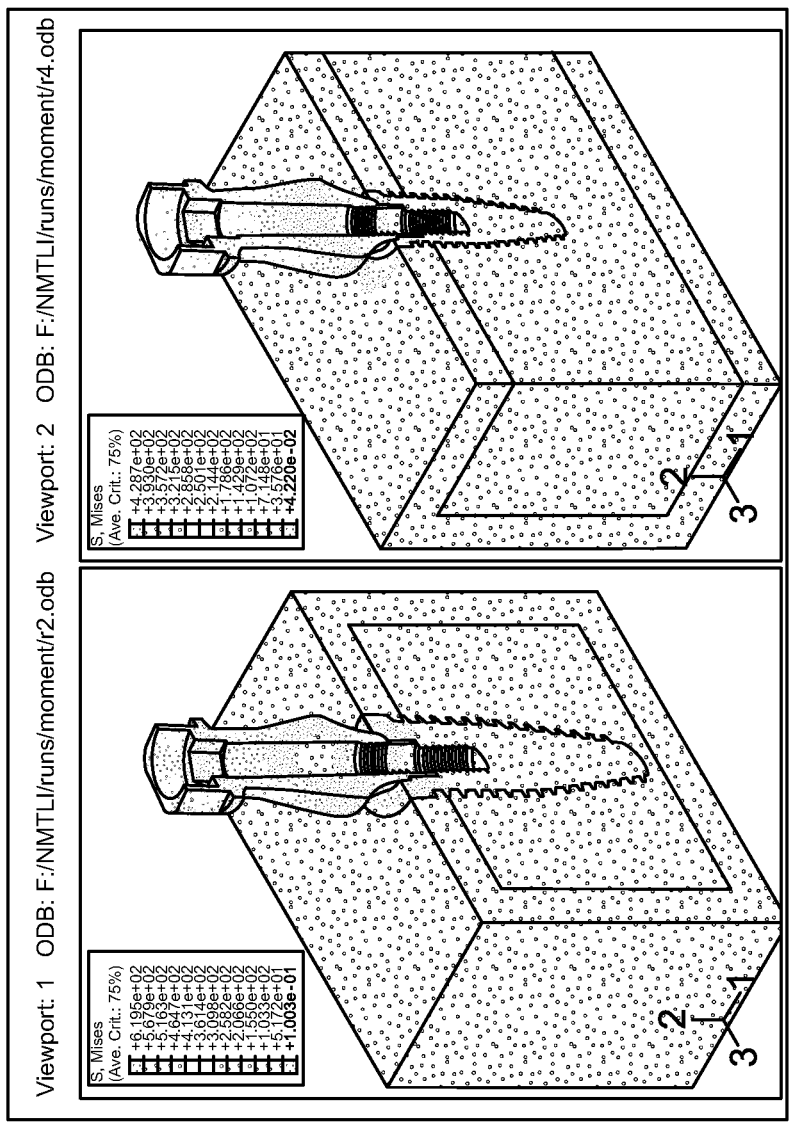
FIG. 20 shows the FEA model of the largest (a) and the smallest dimensions (b) of the implant system with buttress threads under moment type of forces.

In the FEA model, the implant system of the smallest (FIG. 20) and the largest dimension [FIG. 20(a)] was evaluated for the von misses stresses under moment type of forces (450 N). When the moment force was applied on the implant system of largest dimension [FIG. 20 (a)] the von misses stresses at implant abutment junction was recorded as maximum of 317.16 MPa, at the crestal bone level recorded as 153.8 MPa and at corticocancellous interface as 51.7 MPa. When the compression force was applied on the implant system of smallest dimension [FIG. 20 (b)] the von misses stresses at implant abutment junction was recorded as 278.94 MPa, at the crestal bone level recorded as 139.97 MPa and at corticocancellous interface as 30.99 MPa. The von misses stresses generated under moment forces are not uniformly distributed in both the largest and the smallest dimension of implant system. These stresses are much higher than the stresses generated in the compression and tension type of forces. However these are one time forces which would be generated during the placement of the implant system into the bone. Thus the detrimental effects of these stresses are very less and occur only at the initial period of implant placement.

The Example 3, Example 4, and Example 5 showed that Buttress thread design with smallest to the largest dimension implant had developed favorable stress generated in the implant system and the surrounding bone after the application of different type of forces i.e. compression, tension and moment.

The comparison between the smallest (diameter 3.5 and length 10 mm) and the largest dimension (diameter 5 mm and length 13 mm) of the implant fixture in relation to the von misses stresses generated at the different locations of the implant system under compression, tension, and moment type of forces of 450 N, as given in Examples 4, Example 5, and Example 6 is summarized in the Table 1.

The above mentioned table showed that the smallest and the largest dimension implant system under occlusal forces (compression and tension forces) of 450 N yield stresses in the range of 11-37 MPa at the different location of implant abutment assembly (implant system). These stresses generate micostrains in the bone which leads to the favorable bone remodeling as these stresses and strain are in the physiological limits.

TABLE 1

| S. NO. | FORCES & LOCATION | Largest dimension (5 × 13 mm) | Smallest dimension (3.5 × 10 mm) |
|---|---|---|---|
| 1 | COMPRESSION | (N/mm$^2$) | (N/mm$^2$) |
| A) | Implant Abutment interface | 36.51 | 30.94 |
| B) | Crestal bone level | 11.94 | 27.15 |
| C) | Cortico-cancellous interface | 22.59 | 25.33 |
| 2. | TENSION | | |
| A) | Implant Abutment interface | 36.59 | 33.95 |
| B) | Crestal bone level | 22.51 | 27.15 |
| C) | Cortico-cancellous interface | 22.59 | 25.33 |
| 3. | MOMENT | | |
| A) | Implant Abutment interface | 317.16 | 278.94 |
| B) | Crestal bone level | 153.8 | 139.97 |
| C) | Cortico-cancellous interface | 51.7 | 30.99 |

Example 7

The FEA model generated for the complete implant system including implant fixture having different types of thread design (Buttress, Reverse Buttress, Classical V shape and Buttress with micro threads) and multifunctional component with the surrounding cortical and cancellous bone. The model was used for evaluating the effect of compression type of force of about 450 N on the implant system of diameter 3.5 mm and length 10 mm. The evaluation was based on the magnitude and location of von misses stresses at different levels of the implant system.

In the FEA model (FIG. 21), the implant system with different types of thread design i.e. Buttress threads, Reverse buttress threads, Classical V threads, and Buttress threads with micro threads were evaluated for the von misses stresses under compression type of forces (450N).

When the compression force was applied on the implant system with the Revrese buttress threads [FIG. 21 (a)], the von misses stresses generated at the implant abutment junction (in the implant system) was around 36.51 MPa, at the crestal bone level was around 11.94 MPa and at the cortico-cancellous bone interface was around 24.39 MPa.

Figures 21A, 21B, 21C, 21D:
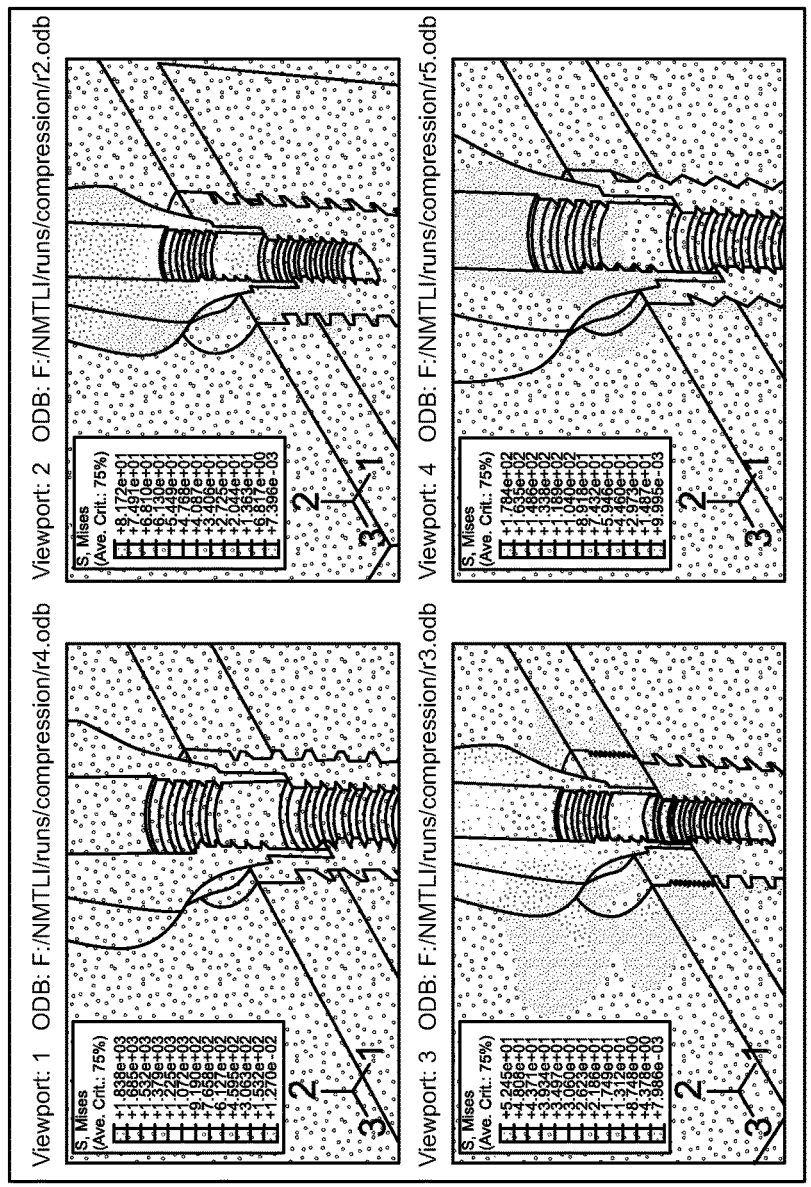
FIG. 21 FEA model of the implant system with different type of thread design viz. Reverse Buttress (a), Buttress (b), Buttress with microthreads (c) and Classical V (d) showing the Von misses stresses generated under compression type of forces.

When the compression force was applied on the implant system with the Buttress threads [FIG. 21(b)], the von misses stresses generated at the implant abutment junction (in the implant system) was around 30.94 MPa, at the crestal bone level was around 20.46 MPa and at the cortico-cancellous bone interface was around 27.25 MPa.

When the compression force was applied on the implant system with the Buttress threads and microthreads [FIG. 21(c)], the von misses stresses generated at the implant abutment junction (in the implant system) was around 38.49 MPa, at the crestal bone level was around 18.48 MPa and at the cortico-cancellous bone interface was around 18.85 MPa.

When the compression force was applied on the implant system with the Classical V threads [FIG. 21 (d)], the von misses stresses generated at the implant abutment junction (in the implant system) was around 41.49 MPa, at the crestal bone level was around 29.71 MPa and at the cortico-cancellous bone interface was around 30.44 MPa.

Example 8

The FEA model generated for the complete implant system including implant fixture having different types of thread design (Buttress, Reverse Buttress, Classical V shape and Buttress with micro threads) and multifunctional component with the surrounding cortical and cancellous bone. The model was used for evaluating the effect of tension type of force of about 450 N on the implant system of diameter 3.5 mm and length 10 mm. The evaluation was based on the magnitude and location of von misses stresses at different levels of the implant system.

In the FEA model (FIG. 22), the implant system with different types of thread design i.e. Buttress threads, Reverse buttress threads, Classical V threads, and Buttress threads with micro threads were evaluated for the von misses stresses under tension type of forces (450N).

When the tension force was applied on the implant system with the Revrese buttress threads (FIG. 22 (a)], the von misses stresses generated at the implant abutment junction (in the implant system) were around 37.57 MPa, at the crestal bone level were around 44.38 MPa and at the cortico-cancellous bone interface were around 63.34 MPa.

When the tension force was applied on the implant system with the Buttress threads [FIG. 22 (b)], the von misses stresses generated at the implant abutment junction (in the implant system) were around 33.95 MPa, at the crestal bone level were around 20.44 MPa and at the cortico-cancellous bone interface were around 27.25 MPa.

When the tension force was applied on the implant system with the Buttress threads and microthreads [FIG. 22 (c)], the von misses stresses generated at the implant abutment junction (in the implant system) were around 38.44 MPa, at the crestal bone level were around 18.48 MPa and at the cortico-cancellous bone interface were around 22.29 MPa.

When the tension force was applied on the implant system with the Classical V threads [FIG. 22 (d)], the von misses stresses generated at the implant abutment junction (in the implant system) were around 40.47 MPa, at the crestal bone level were around 29.73 MPa and at the cortico-cancellous bone interface were around 30.99 MPa.

Example 9

The FEA model generated for the complete implant system including implant fixture having different types of thread design (Buttress, Reverse Buttress, Classical V shape and Buttress with micro threads) and multifunctional component with the surrounding cortical and cancellous bone. The model was used for evaluating the effect of moment type of force of about 450 N on the implant system of diameter 3.5 mm and length 10 mm. The evaluation was based on the magnitude and location of von misses stresses at different levels of the implant system.

In the FEA model (FIG. 23), the implant system with different types of thread design i.e. Buttress threads, Reverse buttress threads, Classical V threads, and Buttress threads with micro threads were evaluated for the von misses stresses under moment type of forces (450N).

When the moment force was applied on the implant system with the Revrese buttress threads [FIG. 23 (a)], the von misses stresses generated at the implant abutment junction (in the implant system) were around 421.62 MPa, at the crestal bone level were around 120.68 MPa and at the cortico-cancellous bone interface were around 9.18 MPa.

When the moment force was applied on the implant system with the Buttress threads [FIG. 23 (b)], the von misses stresses generated at the implant abutment junction (in the implant system) were around 278.94 MPa, at the crestal bone level were around 139.97 MPa and at the cortico-cancellous bone interface were around 30.39 MPa.

When the moment force was applied on the implant system with the Buttress threads and microthreads [FIG. 23 (c)], the von misses stresses generated at the implant abutment junction (in the implant system) were around 396.09 MPa, at the crestal bone level were around 70.27 MPa and at the cortico-cancellous bone interface were around 8.57 MPa.

When the moment force was applied on the implant system with the Classical V threads [FIG. 23 (d)], the von misses stresses generated at the implant abutment junction (in the implant system) were around 425.34 MPa, at the crestal bone level were around 227.03 MPa and at the cortico-cancellous bone interface were around 9.59 MPa.

The comparison between the different thread shapes in relation to the von misses stresses generated at the different locations of the implant system under compression, tension, and moment type of forces (450 N), as given in Examples 7, Example 8, and Example 9 is summarized in the Table 2.

The above mentioned table showed that the Buttress thread and microthread combination under occlusal forces (compression and tension forces) of 450 N yield stresses in the range of 18-39 MPa at the different location of implant abutment assembly (implant system). These stresses generate micostrains in the bone which leads to the favorable bone remodeling as these stresses and strain are in the physiological limits.

TABLE 2

Comparison of different thread types under compression, Tension and moment

| S. No. | PARAMETER & LOCATION | Classical V | Reverse Buttress | Buttress | Buttress & Microthreads |
|---|---|---|---|---|---|
| I) | COMPRESSION | Units-Mpa | | | |
| A) | Implant Abutment interface | 41.49 | 36.51 | 30.94 | 38.49 |
| B) | Crestal bone level | 29.71 | 11.94 | 20.46 | 18.48 |
| C) | Cortico-cancellous interface | 30.44 | 24.39 | 27.25 | 18.85 |
| I) | TENSION | | | | |
| A) | Implant Abutment interface | 40.47 | 37.57 | 33.95 | 38.44 |
| B) | Crestal bone level | 29.73 | 44.38 | 20.44 | 18.48 |
| C) | Cortico-cancellous interface | 30.99 | 63.34 | 27.25 | 22.29 |
| III) | MOMENT | | | | |
| A) | Implant Abutment interface | 425.34 | 421.62 | 278.94 | 396.09 |
| B) | Crestal bone level | 227.03 | 120.68 | 139.97 | 70.27 |
| C) | Cortico-cancellous interface | 9.59 | 9.18 | 30.39 | 8.57 |

Advantages

Advantages of the different components of the implant are as follows:

Dental Implant Fixture is
  screw shaped with external surface having buttress threads on the body and micro threads at the collar of particular dimensions gives the advantage of
    improved biomechanics at the implant abutment interface, self-tapping nature to the implant and minimizes the stresses as supported by FEA, at the crest of the bone leading to decrease resorption of crestal bone during the implant functioning thus ensuring long-term implant stability
    increased surface area which enhances osseointegrated bone implant contact level, have lower stress-shielding effect thus induces better remodeling of bone around implants, favorably transforms and distributes the shearing forces at the bone implant interface and better primary stability.
  having upper cylindrical portion and lower tapering portion gives
    the advantage of self-tapping, easy insertion in the bone, no excessive pressure at the implant bone junction, simulation of the natural anatomy of the root portion of the tooth, and avoiding injury to anatomical structures.

Multifunctional Component
  has a single prosthetic platform
    so one component is compatible with different implant dimensions
      minimizes the inventory needed for the implant system and allows easy handling of the system
  medialised implant abutment junction
  concave transmucosal profile for better esthetics; and
  an additional internal threaded portion for securing abutment screw Abutment Screw
  having internal type interface with medialized implant abutment junction
    allowing better maintenance of crestal bone level
  having external concave transmucosal portion
    enhancing the emergence profile
  having additional internal threads
    for securing the loosened abutment screw.
  having long internal channel
    can be adjusted according to the height of abutment without loosing its fastening property.

We claim:

1. A dental implant system for supporting a prosthetic device wherein the stress values generated by the implant on a jaw bone lie within the physiological limits (1-60 MPa) of bone remodeling, said implant system comprising:
  a dental implant fixture having buttress threads on a body and microthreads on a collar, the dental implant fixture being configured to fix into a bore hole drilled in the jaw bone; and
  a dental multifunctional component configured to be inserted in the dental implant fixture and secured on the dental implant fixture by a dental abutment screw comprising a long internal hex channel in a head portion;
  such that the dental multifunctional component is configured for use as an implant mount, as an impression post and as a final abutment;
  wherein the multifunctional component comprises a medialised implant abutment junction having a concave transmucosal surface extending away from an end of the dental implant fixture and wherein the dental implant and the multifunctional component are configured and adapted so that the medialised implant abutment junction is substantially surrounded by soft tissues when the dental implant and the multifunctional component are assembled together, wherein the concave transmucosal surface contacts soft tissue when the dental implant and the multifunctional component are assembled together to gain a greater volume of soft tissues during healing and a better maintenance of integration with the jaw bone.

2. A dental implant system according to claim 1 wherein the dental multifunctional component comprises:
  an internal threaded portion for securing the abutment screw.

3. A dental implant system according to claim 1 wherein the dental implant fixture comprises:
  a) an upper part having a cylindrical shape with parallel sides and a constant diameter ranging between 5-10% of a total length of the dental implant fixture;
  b) a middle part having a cylindrical shape with parallel sides and a constant diameter ranging between 20-25% of the total length of the dental implant fixture; and
  c) a lower part having a conical shape with tapered sides and a decreasing diameter apically ranging between 60-75% of the total length of the dental implant fixture.

4. A dental implant system according to claim 1 wherein the dental implant fixture has a length in the range of 8-15 mm and a maximum outer diameter of 3.5-6 mm.

5. A dental implant system according to claim 1 wherein the dental implant fixture has a crestal module having a height of 2-3 mm and a top wide flat surface.

6. A dental implant system according to claim 1 wherein the dental implant fixture has a crestal module having a height of 2-3 mm and a surface treated non-threaded collar having a height ranging from 0.4 mm-0.8 mm.

7. A dental implant system according to claim 1 wherein the dental implant fixture has a crestal module with circumferential micro threads, the micro threads having a depth in the range of 50-100 µm, a pitch in the range of 100-150 µm, and a height of 1.2 mm-1.6 mm.

8. A dental implant system according to claim 1 wherein the dental implant fixture has a single lead threaded profile on a middle part and an apical part, the threaded profile covering 70%-90% of a surface of the dental implant fixture.

9. A dental implant system according to claim 1 wherein the dental implant fixture has buttress threads having an upper surface making an angle of 80°-100° to a long axis of the dental implant fixture and a lower bevel surface making an angle of about 110°-135° to the long axis of the dental implant fixture.

10. A dental implant system according to claim 1 wherein the dental implant fixture has buttress threads with a depth in the range of about 0.275-0.375 mm, a pitch in the range of 0.5-0.85 mm and a pitch surface in the range of 100-150 µm.

11. A dental implant system according to claim 1 wherein the dental implant fixture-has an apical part comprising an apical end with a rounded shape and a longitudinal apical recess.

12. A dental implant system according to claim 1 wherein the dental implant fixture has an internal portion extending from a crestal module portion up to a middle portion of the dental implant fixture for connecting the dental implant fixture with the dental multifunctional component and comprising:

a) a leading internal bevel having an angle of 10-20 degrees;
b) an internal hexagonal shape chamber-with a height in the range of 1-2 mm; and
c) a threaded channel of about 2-3 mm.

13. A dental implant system according to claim 1 wherein the dental multifunctional component is capable of functioning as:
    a) an implant mount to transfer the dental implant fixture from a container to the bone site;
    b) an impression post to make an implant level impression; and
    c) a final abutment to place the prosthesis.

14. A dental implant system according to claim 1 wherein the dental multifunctional component has a length to diameter ratio of 3:2.

15. A dental implant system according to claim 1 wherein the dental multifunctional component has a single diameter and a length for different diameters of the dental implant fixture.

16. A dental implant system according to claim 1 wherein the dental multifunctional component has a diameter that is smaller than a top surface of the dental implant fixture, thus medialising an implant-abutment junction.

17. A dental implant system according to claim 1 wherein the dental multifunctional component comprises:
    a) an upper portion which is 10-20% of a total length of the dental multifunctional component;
    b) a middle portion which is 60-70% of the total length of the dental multifunctional component; and
    c) a lower portion which is 20-30% of the total length of the dental multifunctional component.

18. A dental implant system according to claim 17 wherein the dental multifunctional component has an internal channel of decreasing diameter of 3.5 mm to 1.85 mm from the upper portion, to the middle portion and to the lower portion.

19. A dental implant system according to claim 1 wherein the dental multifunctional component comprises an upper portion having a square shaped head configured to engage a hand ratchet while screwing the implant fixture into the bone and a perpendicular flange having an undercut surface for the retention of impression material.

20. A dental implant system according to claim 1 wherein the dental multifunctional component has an upper portion configured to be cut during the preparation or customized milling of the final abutment from the multifunctional component.

21. A dental implant system according to claim 1 wherein the dental multifunctional component has a middle portion comprising annular grooves and horizontal lines.

22. A dental implant system according to claim 1 wherein the dental multifunctional component is having middle portion consisting of flat cut surface with the window shape design, the base which is parallel to one of the side of the hexagonal shaped internal chamber of the implant fixture, thus determines the proper orientation of the implant during surgery and aids in prosthetic procedures.

23. A dental implant system according to claim 1 wherein the dental multifunctional component has a lower portion consisting of a concave transmucosal part which gives an esthetical emergence profile to a prosthesis placed over the dental multifunctional component.

24. A dental implant system according to claim 1 wherein the dental multifunctional component is having an additional threaded portion in the lower part of the internal channel which helps in securing the abutment screw and prevents screw loosening and prevents the falling of abutment screw in an oral cavity while getting it disengaged from the implant fixture internal channel in the initial prosthetic procedures.

25. A dental implant system according to claim 1 wherein the dental abutment screw has a length ranging from 11-19 mm and comprises:
    a) an upper head portion having a length that is 25% to 40% of the total length of the dental abutment screw;
    b) a middle shaft portion having a length that is 30% to 60% of the total length of the dental abutment screw; and
    c) a lower threaded portion having a length that is 15% to 30% of the total length of the dental abutment screw.

26. A dental implant system according to claim 1 wherein the dental abutment screw is having has upper, middle and lower portions in the ratio of 25%: 60%: 15% respectively.

27. A dental implant system according to claim 1 wherein the dental abutment screw has an internal portion with a hexagonal channel, the hexagonal channel has-size 0.70-0.80 mm wide and 4-5 mm deep.

28. A dental implant system according to claim 1 wherein the said implant system yields stresses in the range of 18-39 MPa, at an implant abutment junction, a crestal area and a cortico-cancelous junction of the implant system, under compression type of forces of 450N.

29. A dental implant system according to claim 1, wherein the said implant system yields stresses in the range of 18-39 MPa, at an implant abutment junction, a crestal area and a cortico-cancelous junction of the implant system, under tension type of forces of 450N.

30. A dental implant system according to claim 28 or 29, wherein the stresses are calculated using finite element analysis.

31. A dental implant system according to claim 1, wherein the dental implant fixture is configured to be screwed into a bore drilled into a tooth less-site in a maxilla or mandible jaw bone, on which the dental multifunctional component is inserted and fixed by the dental abutment screw.

32. The dental implant system of claim 1, wherein the implant fixture includes an internal portion that the multifunctional component partially fits into, wherein the internal portion includes a leading internal bevel, wherein the multifunctional component includes a beveled surface that mates with the leading internal bevel of the implant fixture, wherein the concave transmucosal surface extends upward from the beveled surface of the multifunctional component, wherein concave transmucosal surface flushly emanates from the internal portion of the implant fixture.

33. A method of supporting a prosthetic device on a dental implant system, comprising the steps of:
    fixing a dental implant fixture having buttress threads on a body and micro threads on the collar into a bore hole drilled in a jaw bone;
    inserting a dental multifunctional component in the dental implant fixture;
    securing the dental multifunctional component in place by a dental abutment screw having a long internal hex channel in a head portion; and
    supporting the prosthetic device on the dental multifunctional component
        wherein the multifunctional component comprises a medialised implant abutment junction having a concave transmucosal surface extending away from an end of the dental implant fixture and wherein the dental implant and the multifunctional component are configured and adapted so that the medialised implant abutment junction is substantially surrounded by soft tissues when the dental implant and the multifunctional component are assembled together, wherein the concave transmucosal surface contacts soft tissue when the dental implant and the multifunctional component are assembled together to gain a greater volume of soft tissues during healing and a better maintenance of integration with the jaw bone.

* * * * *